US012144815B2

(12) United States Patent
Knie

(10) Patent No.: US 12,144,815 B2
(45) Date of Patent: Nov. 19, 2024

(54) USE OF APREPITANT FOR TREATING ALZHEIMER'S DISEASE

(71) Applicant: Hoth Therapeutics, Inc., New York, NY (US)

(72) Inventor: Robb Knie, Fort Lee, NJ (US)

(73) Assignee: Hoth Therapeutics, Inc., New York, NY (US)

( * ) Notice: Subject to any disclaimer, the term of this patent is extended or adjusted under 35 U.S.C. 154(b) by 0 days.

(21) Appl. No.: 17/677,698

(22) Filed: Feb. 22, 2022

(65) Prior Publication Data

US 2022/0265672 A1    Aug. 25, 2022

Related U.S. Application Data

(60) Provisional application No. 63/152,458, filed on Feb. 23, 2021.

(51) Int. Cl.
| | | |
|---|---|---|
| A61K 31/5377 | (2006.01) | |
| A61K 31/192 | (2006.01) | |
| A61K 31/27 | (2006.01) | |
| A61K 31/407 | (2006.01) | |
| A61K 31/415 | (2006.01) | |
| A61K 31/4425 | (2006.01) | |
| A61K 31/4439 | (2006.01) | |
| A61K 31/445 | (2006.01) | |
| A61K 31/5365 | (2006.01) | |
| A61K 31/675 | (2006.01) | |
| A61K 31/683 | (2006.01) | |
| A61K 39/395 | (2006.01) | |
| A61P 25/28 | (2006.01) | |

(52) U.S. Cl.
CPC ........ *A61K 31/5377* (2013.01); *A61K 31/192* (2013.01); *A61K 31/27* (2013.01); *A61K 31/407* (2013.01); *A61K 31/415* (2013.01); *A61K 31/4425* (2013.01); *A61K 31/4439* (2013.01); *A61K 31/445* (2013.01); *A61K 31/5365* (2013.01); *A61K 31/675* (2013.01); *A61K 31/683* (2013.01); *A61K 39/3955* (2013.01); *A61P 25/28* (2018.01)

(58) Field of Classification Search
CPC ....................................................... A61P 25/28
See application file for complete search history.

(56) References Cited

U.S. PATENT DOCUMENTS

| | | | |
|---|---|---|---|
| 4,144,317 A | 3/1979 | Higuchi | |
| 5,750,349 A | 5/1998 | Suzuki | |
| 5,750,549 A | 5/1998 | Caldwell | |
| 5,797,898 A | 8/1998 | Santini | |
| 6,027,896 A | 2/2000 | Roses | |
| 6,174,884 B1 | 1/2001 | Haning | |
| 6,235,742 B1 | 5/2001 | Bell | |
| 7,107,092 B2 | 9/2006 | Goldstein | |
| 7,115,600 B2 | 10/2006 | Wager | |
| 7,285,293 B2 | 10/2007 | Castillo | |
| 8,124,633 B2 | 2/2012 | Devita | |
| 9,518,101 B2 | 12/2016 | Novak | |
| 2003/0073655 A1 | 4/2003 | Chain | |
| 2003/0195205 A1 | 10/2003 | Deninno | |
| 2004/0192898 A1 | 9/2004 | Jia | |
| 2004/0220186 A1 | 11/2004 | Bell | |
| 2005/0019328 A1 | 1/2005 | Schenk | |
| 2005/0043354 A1 | 2/2005 | Wager | |
| 2005/0048049 A1 | 3/2005 | Schenk | |
| 2005/0256135 A1 | 11/2005 | Lunn | |
| 2005/0267095 A1 | 12/2005 | Bernardelli | |
| 2006/0106035 A1 | 5/2006 | Hendrix | |
| 2006/0111372 A1 | 5/2006 | Hendrix | |
| 2007/0031416 A1 | 2/2007 | Shoji | |
| 2008/0096955 A1 | 4/2008 | Wager | |
| 2008/0176925 A1 | 7/2008 | Butler | |
| 2009/0030003 A1 | 1/2009 | Verhoest | |
| 2010/0209496 A1 | 8/2010 | Dokou | |
| 2011/0201597 A1* | 8/2011 | Chase | A61K 31/166 514/319 |
| 2014/0193526 A1 | 7/2014 | Henry | |
| 2016/0143890 A1 | 5/2016 | Chase | |
| 2018/0296564 A1 | 10/2018 | Vink | |
| 2020/0197404 A1 | 6/2020 | Ottoboni | |
| 2021/0393595 A1* | 12/2021 | Chase | A61K 45/06 |

FOREIGN PATENT DOCUMENTS

| | | |
|---|---|---|
| WO | WO1998/044955 | 10/1998 |
| WO | WO2001/062801 | 8/2001 |
| WO | WO2002/020521 | 3/2002 |

(Continued)

OTHER PUBLICATIONS

Stages of Alzheimer's Disease John Hopkins Medicine https://www.hopkinsmedicine.org/health/conditions-and-diseases/alzheimers-disease/stages-of-alzheimer-disease (Year: 2020).*

Brain Imaging in Alzheimer Disease Johnson et al. Cold Spring Harb Perspect Med 2012;2:a006213 (Year: 2012).*

Early Onset Familial AD Gabrielle Strobel https://www.alzforum.org/early-onset-familial-ad/overview/what-early-onset-familial-alzheimer-disease-efad#:~:text=Like%20the%20more%20common%20late,to%20slow%20down%20the%20disease. (Year: 2020).*

(Continued)

*Primary Examiner* — Jeffrey S Lundgren
*Assistant Examiner* — Eric Tran
(74) *Attorney, Agent, or Firm* — Dickinson Wright PLLC

(57) ABSTRACT

Disclosed herein include methods, compositions, and kits suitable for use in preventing and treating Alzheimer's disease. In some embodiments, methods of delaying or reducing the likelihood of onset of Alzheimer's disease are provided. The method can comprise administering to a subject in need thereof a composition comprising a neurokinin 1 receptor (NK1R) antagonist (e.g., aprepitant).

27 Claims, 4 Drawing Sheets

(56) References Cited

FOREIGN PATENT DOCUMENTS

| | | |
|---|---|---|
| WO | WO2004/032868 | 4/2004 |
| WO | WO2005/049616 | 6/2005 |
| WO | WO2006/036291 | 4/2006 |
| WO | WO2006/069081 | 6/2006 |
| WO | WO2006/118959 | 11/2006 |
| WO | WO2006/120552 | 11/2006 |
| WO | WO2006/126081 | 11/2006 |
| WO | WO2006/126082 | 11/2006 |
| WO | WO2006/126083 | 11/2006 |
| WO | WO2006/136924 | 12/2006 |
| WO | WO2007/063385 | 6/2007 |
| WO | WO2007/069053 | 6/2007 |
| WO | WO2007/088450 | 8/2007 |
| WO | WO2007/088462 | 8/2007 |
| WO | WO2007/099423 | 9/2007 |
| WO | WO2007/105053 | 9/2007 |
| WO | WO2007/122466 | 11/2007 |
| WO | WO2007/138431 | 12/2007 |

OTHER PUBLICATIONS

The Therapeutic Potential of Targeting Substance P/NK-1R Interactions in Inflammatory CNS Disorders Johnson et al. Front. Cell. Neurosci., Jan. 4, 2017 (Year: 2017).*

A Survey of Alzheimer's Disease Early Diagnosis Methods for Cognitive Assessment Montenegro et al. Sensors 2020, 20, 7292; doi:10.3390/s20247292 (Year: 2020).*

Neurokinin-1 receptor inhibition reverses ischaemic brain injury and dementia in bilateral common carotid artery occluded rats: possible mechanisms Kaur et al. Inflammopharmacol (2016) 24:133-143 (Year: 2016).*

Long-Term Daily Administration of Aprepitant for the Management of Intractable Nausea and Vomiting in Children With Life-Limiting Conditions: A Case Series Patel et al. Journal of Pain and Symptom Management, vol. 62 No. 3 (Year: 2021).*

International Search Report and Written Opinion dated May 2, 2022 in PCT Patent Application No. PCT/US2022/017320.

Albert et al., "The diagnosis of mild cognitive impairment due to Alzheimer's disease: recommendations from the National Institute on Aging-Alzheimer's Association workgroups on diagnostic guidelines for Alzheimer's disease," Alzheimers Dement 2011, 7(3), 270-279.

Berczi et al., "Neuropeptides in Immunoregulation," Insights to Neuroimmune Biology 2016, 133-181.

Bertram et al., "Is α-T catenin (VR22) an Alzheimer's disease risk gene?," Journal of Medical Genetics 2007, 44(1), in 4 pages.

Bertram et al., "Systematic meta-analyses of Alzheimer disease genetic association studies: the AlzGene database," Nature Genetics 2007, 39(1), 17-23.

Burns et al., "Alzheimer's disease," The Lancet 2002, 360(9327), 163-165.

Cirrito et al., "In vivo assessment of brain interstitial fluid with microdialysis reveals plaque-associated changes in amyloid-β metabolism and half-life," Journal of Neuroscience 2003, 23(26), 8844-8853.

Cummings et al., "Alzheimer's disease drug development pipeline: 2017," Alzheimer's & Dementia: Translational Research & Clinical Interventions 2017, 3(3), 367-384.

Cutler et al., "Cerebrospinal fluid neuron-specific enolase is reduced in Alzheimer's disease," Archives of Neurology 1986, 43(2), 153-154.

Folstein et al., ""Mini-mental state": a practical method for grading the cognitive state of patients for the clinician," Journal of Psychiatric Research 1975, 12(3), 189-198.

Gibson et al., "CSF monoamine metabolite levels in Alzheimer's and Parkinson's disease," Archives of Neurology 1985, 42(5), 489-492.

Goldstein et al., "Cytosolic β-amyloid deposition and supranuclear cataracts in lenses from people with Alzheimer's disease," The Lancet 2003, 361(9365), 1258-1265.

Hettinger et al., "AMPA-ergic regulation of amyloid-β levels in an Alzheimer's disease mouse model," Molecular Neurodegeneration 2018, 13(1), in 17 pages.

Jagust et al., "Longitudinal studies of regional cerebral metabolism in Alzheimer's disease," Neurology 1988, 38(6), 909-912. Abstract Only.

Johnson et al., "The therapeutic potential of targeting substance P/NK-1R interactions in inflammatory CNS disorders," Frontiers in Cellular Neuroscience 2017, 10, in 14 pages.

Khachaturian, "Diagnosis of Alzheimer's disease," Archives of Neurology 1985, 42(11), 1097-1105.

Kim et al., "Decreased catalytic activity of the insulin-degrading enzyme in chromosome 10-linked Alzheimer disease families," Journal of Biological Chemistry 2007, 282(11), 7825-7832.

Martinez & Philipp, "Substance P and antagonists of the neurokinin-1 receptor in neuroinflammation associated with infectious and neurodegenerative diseases of the central nervous system," Journal of Neurology & Neuromedicine 2016, 1(2), 29-36.

McKhann et al., "Clinical diagnosis of Alzheimer's disease: Report of the NINCDS-ADRDA Work Group* under the auspices of Department of Health and Human Services Task Force on Alzheimer's Disease," Neurology 1984, 34(7), 939-944.

Nema & Brendel, "Excipients and their role in approved injectable products: current usage and future directions," PDA Journal of Pharmaceutical Science and Technology 2011, 65(3), 287-332.

Powell et al., "Compendium of excipients for parenteral formulations," PDA Journal of Pharmaceutical Science and Technology 1998, 52(5), 238-311. Abstract Only.

Prohovnik et al., "Cerebral perfusion as a diagnostic marker of early Alzheimer's disease," Neurology 1988, 38(6), 931-937. Abstract Only.

Rogaeva et al., "The neuronal sortilin-related receptor SORL1 is genetically associated with Alzheimer disease," Nature Genetics 2007, 39(2), 168-177.

Sloane et al., "The public health impact of Alzheimer's disease, 2000-2050: potential implication of treatment advances," Annual Review of Public Health 2002, 23(1), 213-231.

St George-Hyslop et al., "The genetic defect causing familial Alzheimer's disease maps on chromosome 21," Science 1987, 235(4791), 885-890.

Tamminga et al., "Alzheimer's disease: low cerebral somatostatin levels correlate with impaired cognitive function and cortical metabolism," Neurology 1987, 37(1), 161-161. Abstract Only.

Ubaldi et al., "Emerging targets for addiction neuropharmacology: from mechanisms to therapeutics," Progress in Brain Research 2016, 224, 251-284.

Volicer et al., "Serotonin and 5-hydroxyindoleacetic acid in CSF: difference in Parkinson's disease and dementia of the Alzheimer's type," Archives of Neurology 1985, 42(2), 127-129.

Wolozin & Davies, "Alzheimer related protein A68: specificity and distribution," Annals of Neurology 1987, 22(4), 521-526.

Wolozin et al., "A neuronal antigen in the brains of Alzheimer patients," Science 1986, 232(4750), 648-650.

* cited by examiner

USE OF APREPITANT FOR TREATING ALZHEIMER'S DISEASE

CROSS-REFERENCE TO RELATED APPLICATIONS

This application claims the benefit under 35 U.S.C. § 119(e) to U.S. Provisional Patent Application No. 63/152,458 filed on Feb. 23, 2021. The content of this related applications is incorporated herein by reference in its entirety for all purposes.

BACKGROUND

Field

The present disclosure relates generally to the fields of neurobiology, molecular biology and medicine. One aspect relates to the treatment and prevention of Alzheimer's disease with a neurokinin 1 receptor (NK1R) antagonist (e.g., aprepitant).

Description of the Related Art

Alzheimer's disease (AD) is a progressive neurodegenerative disorder that is associated with the destruction of higher brain structures, such as those involved in memory and cognition. The disease leads to deficits in cognitive function and declines in memory, learning, language, and in the ability to perform intentional and purposeful movements. AD is also accompanied by concomitant behavioral, emotional, interpersonal, and social deterioration. These cognitive and behavioral deficits render living difficult (Burns et al., Alzheimer's disease, The Lancet, vol. 360, Jul. 13, 2002). Late-stage AD patients are often unable to speak, comprehend language, and handle their own basic personal care, eventually requiring full-time care and supervision, and are often dependent on family members and nursing homes. AD is the leading cause of senile dementia, and is predicted to increase in prevalence as the proportion of elderly persons in the population grows. The total number of persons with AD is predicted to increase at least threefold between 2000 and 2050, rendering AD a world-wide public health problem (Sloane et al., The Public Health Impact of Alzheimer's Disease, 2000-2050: Potential Implication of Treatment Advances, Annu. Rev. Public Health, 23:213-31 , 2002). Clinical detection, management, and treatment of AD remains largely inadequate. There is still an unmet need for effective methods to prevent and treat AD.

Histopathologically, AD can be characterized by the accumulation of amyloid plaques comprising the amyloid-β (Aβ) peptide and neurofibrillary tangles (NFTs) made of the tau protein. Under normal conditions, the soluble AP peptide is produced and secreted by neurons and subsequently cleared from the brain via cerebral spinal fluid (CSF) pathways. However, in subjects with AD, the Aβ peptide appears to aggregate into higher-order species to form soluble oligomers and insoluble plaques in a concentration-dependent manner. This aggregation may initiate many neurotoxic events including disrupted brain metabolism, neuroinflammation, reduced functional connectivity, synaptic and neuronal loss, and/or formation of NFTs.

Currently AD has no cure, and treatment options do not inhibit the pathological progression of AD, are mainly palliative, and/or may have multiple, troubling side effects. For example, preventative and/or therapeutic strategies targeting the Aβ peptide and/or its precursors (e.g., Aβ immunotherapy and inhibition of β- and γ-secretases) have been toxic and/or ineffective at reducing AD pathology in clinical trials. Clinical trials involving amyloid beta vaccines (e.g., bapineuzumab) have failed due to lack of cognitive benefit. Gamma-secretase inhibitors (e.g., semagacestat) have failed clinical trials for worsening of cognitive deficits in subjects. Even existing medications like acetylcholinesterase inhibitors (e.g., donepezil and rivastigmine) and N-methyl-D-aspartate (NMDA)-receptor antagonists (e.g., memantine) demonstrate only mild cognitive benefits. There is an urgent need for effective treatments for AD. Compositions and methods for delaying or reducing the likelihood of onset of Alzheimer's disease are also urgently needed.

SUMMARY

Disclosed herein are methods for treating Alzheimer's disease (AD). In some embodiments, the method comprises: administering to a subject in need thereof a composition comprising a NK1R antagonist (e.g., aprepitant) or a pharmaceutically acceptable salt, solvate, stereoisomer, or prodrug thereof.

Disclosed herein are methods for delaying or reducing the likelihood of onset of AD. In some embodiments, the method comprises: administering to a subject in need thereof a composition comprising a NK1R antagonist (e.g., aprepitant) or a pharmaceutically acceptable salt, solvate, stereoisomer, or prodrug thereof, thereby delaying or reducing the likelihood of onset of AD in the subject. In some embodiments, the subject in need thereof is not administered with the NK1R antagonist and any additional therapeutical agent for neurological disorders on the same day or within a two-, three-, or four-day period. In some embodiments, the subject in need thereof is not administered with the NK1R antagonist and any additional therapeutical agent for neurological disorders within a one-hour, two-hour, three-hour, four-hour, five-hour, six-hour, seven-hour, eight-hour, nine-hour, twelve-hour, thirteen-hour, fourteen-hour, fifteen-hour, sixteen-hour, seventeen-hour, eighteen-hour, nineteen-hour, twenty-hour, twenty-one-hour, twenty-two-hour, twenty-three-hour, or twenty-four hour, period.

Disclosed herein are methods for treating, preventing, or reversing cognitive decline in clinical or pre-clinical AD. In some embodiments, the method comprises: administering to a subject in need thereof a composition comprising a NK1R antagonist (e.g., aprepitant) or a pharmaceutically acceptable salt, solvate, stereoisomer, or prodrug thereof. In some embodiments, the subject in need thereof is not administered with the NK1R antagonist and any additional therapeutical agent for neurological disorders on the same day or within a two-, three-, or four-day period. In some embodiments, the subject in need thereof is not administered with the NK1R antagonist and any additional therapeutical agent for neurological disorders within a one-hour, two-hour, three-hour, four-hour, five-hour, six-hour, seven-hour, eight-hour, nine-hour, twelve-hour, thirteen-hour, fourteen-hour, fifteen-hour, sixteen-hour, seventeen-hour, eighteen-hour, nineteen-hour, twenty-hour, twenty-one-hour, twenty-two-hour, twenty-three-hour, or twenty-four hour, period.

Disclosed herein are methods for delaying or reversing the progression of AD. In some embodiments, the method comprises: administering to a subject in need thereof a composition comprising a NK1R antagonist (e.g., aprepitant) or a pharmaceutically acceptable salt, solvate, stereoisomer, or prodrug thereof. In some embodiments, the subject in need thereof is not administered with the NK1R antagonist and any additional therapeutical agent for neurological disorders on the same day or within a two-, three-, or four-day period. In some embodiments, the subject in need thereof is not administered with the NK1R antagonist and any additional therapeutical agent for neurological disorders within a one-hour, two-hour, three-hour, four-hour, five-hour, six-hour, seven-hour, eight-hour, nine-hour, twelve-hour, thirteen-hour, fourteen-hour, fifteen-hour, sixteen-hour, seventeen-hour, eighteen-hour, nineteen-hour, twenty-hour, twenty-one-hour, twenty-two-hour, twenty-three-hour, or twenty-four hour, period.

In some embodiments, the composition comprises a therapeutically or prophylactically effective amount of a NK1R antagonist (e.g., aprepitant) or a pharmaceutically acceptable salt, solvate, stereoisomer, or prodrug thereof. In some embodiments, the subject is a mammal. In some embodiments, the subject is a human. In some embodiments, said subject is a human over 40 years old, over 50 years old, over 60 years old, over 65 years old, over 70 years old, over 80 years old, and/or over 85 years old. In some embodiments, the subject in need thereof has mild cognitive impairment related to AD, has AD, is suspected of having AD, or is at a risk of having AD. In some embodiments, said subject is diagnosed with mild cognitive impairment related to AD, early stage AD, mid-stage AD, and/or late-stage AD. In some embodiments, said AD is sporadic (non-hereditary) AD. In some embodiments, said AD is familial (hereditary) AD. The subject is a ApoE e4 allele carrier, in some embodiments. The method disclosed herein can, in some embodiments, comprise identifying the subject for treatment as a subject who is an ApoE e4 allele carrier.

The composition can be a pharmaceutical composition comprising a NK1R antagonist (e.g., aprepitant) or a pharmaceutically acceptable salt, solvate, stereoisomer, or prodrug thereof, and one or more pharmaceutically acceptable excipients. In some embodiments, the composition is administered to the subject by intravenous administration, nasal administration, pulmonary administration, oral administration, parenteral administration, or nebulization. In some embodiments, the composition is administered to the subject by oral or intravenous administration. In some embodiments, the composition is in the form of powder, pill, tablet, microtablet, pellet, micropellet, capsule, capsule comprising microtablets, film, oral disintegrating tablet, liquid, aerosols, or nanoparticles. In some embodiments, the composition is administered to the subject once, twice, or three times a day. In some embodiments, the composition is administered to the subject once every day, every two days, or every three days. In some embodiments, the composition is administered to the subject at an effective daily dose of a NK1R antagonist (e.g., aprepitant) or a pharmaceutically acceptable salt, solvate, stereoisomer, or prodrug thereof at from 10 mg to 250 mg.

The composition can further comprise one or more additional therapeutic agents. The method can, in some embodiments, further comprise administering to said subject, concurrently or sequentially, an effective amount of at least one additional therapeutic agent.

In some embodiments, administering the composition reduces formation of plaques. In some embodiments, administering the composition reduces amyloid fibril formation. In some embodiments, administering the composition reduces amyloid-induced cellular toxicity or microglial activation. In some embodiments, administering the composition reduces amyloid-induced neurotoxicity. In some embodiments, administering the composition reduces the rate or amount of amyloid aggregation, fibril formation, or deposition. In some embodiments, administering the composition lessens the degree of amyloid deposition. In some embodiments, administering the composition reduces amyloid-induced inflammation. In some embodiments, administering the composition results in reduction of neuroinflammation. In some embodiments, administering the composition reduces or slows down the formation of tangles containing hyperphosphorylated tau. In some embodiments, administering the composition reduces the concentration or the amount of phosphorylated tau. In some embodiments, the reduction of neuroinflammation comprises changes in one or more of cell signaling molecule production, activation of glia or glial activation pathways and responses, proinflammatory cytokines or chemokines, oxidative stress-related responses, acute phase proteins, components of the complement cascade, protein kinase activity, cell damage and cell death signal transduction pathways.

The method can comprise measuring one or more AD symptom in the subject before administering the composition to the subject, after administering the composition to the subject, or both. In some embodiments, administering the composition treats, prevents, improves, and/or resolves one or more AD symptom. In some embodiments, administering the composition treats, prevents, improves, and/or resolves one or more AD symptom by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%. In some embodiments, the progression or onset of AD is slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, optionally the progression or onset of AD is evaluated by measuring one or more symptoms of AD. In some embodiments, the progression or onset of AD is measured quantitatively or qualitatively by one or more techniques selected from the group comprising electroencephalogram (EEG), neuroimaging, functional Mill, structural Mill, diffusion tensor imaging (DTI), [18F] fluorodeoxyglucose (FDG) PET, agents that label amyloid, [18F]F-dopa PET, radiotracer imaging, volumetric analysis of regional tissue loss, specific imaging markers of abnormal protein deposition, multimodal imaging, biomarker analysis, or any combination thereof.

In some embodiments, the AD symptom is one or more of: (a) a symptom from the Integrated Alzheimer's Disease Rating Scale (iADRS) selected from personal belonging management, selection of clothes, ability to dress self, ability to clean habitation, financial management ability, writing ability, ability to keep appointments, ability to use telephone, ability to prepare food for self, travel ability, awareness of current events, reading ability, interest in television, ability to shop for self, ability to remain alone, ability to perform chores, ability to perform a hobby or game, driving ability, self-management of medications, ability to initiate and finish complex tasks, and ability to initiate and finish simple tasks; (b) a symptom from the Alzheimer's Disease Assessment Scale-Cognitive subscale (ADAS-Cog) selected from learning, naming, command following, ideational praxis, constructional praxis, orientation, and recognition memory; (c) a symptom from the Alzheimer's Disease Cooperative Study-instrumental Activities of Daily Living (ADCS-iADL) wherein the symptom is any of the symptoms recited in (a) or (b); (d) constipation; (e) depression; (f)

cognitive impairment; (g) short term memory impairment; (h) long term memory impairment; (i) concentration impairment; (j) coordination impairment; (k) mobility impairment; (l) speech impairment; (m) mental confusion; (n) sleep problem, sleep disorder, or sleep disturbance; (o) circadian rhythm dysfunction; (p) REM disturbed sleep; (q) REM behavior disorder; (r) hallucinations; (s) fatigue; (t) apathy; (u) erectile dysfunction; (v) mood swings; (w) urinary incontinence; (x) mild cognitive impairment; and (w) neurodegeneration.

In some embodiments, the AD symptom is a sleep problem, sleep disorder, sleep disturbance, circadian rhythm dysfunction, REM disturbed sleep, or REM behavior disorder. In some embodiments, the sleep disorder or sleep disturbance comprises a delay in sleep onset, sleep fragmentation, REM-behavior disorder, sleep-disordered breathing including snoring and apnea, daytime sleepiness, microsleep episodes, narcolepsy, hallucinations, or any combination thereof. In some embodiments, the REM-behavior disorder comprises vivid dreams, nightmares, and acting out the dreams by speaking or screaming, or fidgeting or thrashing of arms or legs during sleep. In some embodiments, the method results in a positive change in the sleeping pattern of the subject over a defined period of time. In some embodiments, the method results in a positive change in the sleeping pattern of the subject over a defined period of time, wherein the positive change is defined as: (i) an increase in the total amount of sleep obtained of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%; and/or (ii) a percent decrease in the number of awakenings during the night selected from about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, or a range or a number between any two of these values. In some embodiments, as a result of the method the subject obtains the total number of hours of sleep recommended by a medical authority for the age group of the subject. In some embodiments, each defined period of time is independently selected from about 1 day to about 10 days, about 10 days to about 30 days, about 30 days to about 3 months, about 3 months to about 6 months, about 6 months to about 12 months, and about greater than 12 months.

In some embodiments, the AD symptom is a hallucination(s). In some embodiments, the hallucination comprises a visual, auditory, tactile, gustatory or olfactory hallucination. In some embodiments, the method results in a decreased number of hallucinations over a defined period of time in the subject. In some embodiments, the method results in a decreased number of hallucinations over a defined period of time in the subject selected from a decrease by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%. In some embodiments, the method results in the subject being hallucination-free. In some embodiments, the method results in a decreased severity of hallucinations in the subject over a defined period of time, wherein the decrease in severity is measured by one or more medically-recognized techniques. In some embodiments, the method results in a decreased severity of hallucinations in the subject over a defined period of time, wherein the decrease in severity is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, as measured by one or more medically recognized techniques. In some embodiments, the one or more medically recognized techniques is selected from Chicago Hallucination Assessment Tool (CHAT), The Psychotic Symptom Rating Scales (PSYRATS), Auditory Hallucinations Rating Scale (AHRS), Hamilton Program for Schizophrenia Voices Questionnaire (HPSVQ), Characteristics of Auditory Hallucinations Questionnaire (CAHQ), Mental Health Research Institute Unusual Perception Schedule (MUPS), positive and negative syndrome scale (PANSS), scale for the assessment of positive symptoms (SAPS), Launay-Slade hallucinations scale (LSHS), the Cardiff anomalous perceptions scale (CAPS), and structured interview for assessing perceptual anomalies (SIAPA). In some embodiments, each defined period of time is independently selected from about 1 day to about 10 days, about 10 days to about 30 days, about 30 days to about 3 months, about 3 months to about 6 months, about 6 months to about 12 months, and about greater than 12 months.

In some embodiments, the AD symptom is depression. In some embodiments, the method results in improvement in the subject's depression over a defined period of time, as measured by one or more clinically-recognized depression rating scale. In some embodiments, the method results in improvement in the subject's depression over a defined period of time, as measured by one or more clinically-recognized depression rating scale and the improvement is in one or more depression characteristics selected from mood, behavior, bodily functions such as eating, sleeping, energy, and sexual activity, and/or episodes of sadness or apathy. In some embodiments, the method results in improvement in the subject's depression over a defined period of time, as measured by one or more clinically-recognized depression rating scale, and the improvement a subject experiences following treatment is about 5, about 10, about 15, about 20, about 25, about 30, about 35, about 40, about 45, about 50, about 55, about 60, about 65, about 70, about 75, about 80, about 85, about 90, about 95 or about 100%. In some embodiments, each defined period of time is independently selected from about 1 day to about 10 days, about 10 days to about 30 days, about 30 days to about 3 months, about 3 months to about 6 months, about 6 months to about 12 months, and about greater than 12 months.

In some embodiments, the AD symptom is cognitive impairment, for example mild cognitive impairment (MCI). In some embodiments, progression or onset of the cognitive impairment is slowed, halted, or reversed over a defined period of time following administration of the composition, as measured by a medically-recognized technique. In some embodiments, the cognitive impairment is positively impacted by the administered composition, as measured by a medically-recognized technique. In some embodiments, the cognitive impairment is positively impacted by the administered composition, as measured by a medically-recognized technique and the positive impact on and/or progression of cognitive impairment is measured quantitatively or qualitatively by one or more techniques selected from Mini-Mental State Exam (MMSE), Mini-cog test, and a computerized test selected from Cantab Mobile, Cognigram, Cognivue, Cognision, or Automated Neuropsychological Assessment Metrics. In some embodiments, the progression or onset of cognitive impairment is slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique. In some embodiments, each defined period of time is independently selected from about 1 day to about 10 days, about 10 days to about 30 days, about 30 days to about 3 months, about 3 months to about 6 months, about 6 months to about 12 months, and about greater than 12 months.

In some embodiments, the AD symptom is constipation. In some embodiments, the composition causes the subject to have a bowel movement. In some embodiments, the method results in an increase in the frequency of bowel movement in the subject. In some embodiments, the method results in an increase in the frequency of bowel movement in the subject and the increase in the frequency of bowel movement is defined as: (i) an increase in the number of bowel movements per week of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%; and/or (ii) a percent decrease in the amount of time between each successive bowel movement selected from about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In some embodiments, as a result of the method the subject has the frequency of bowel movement recommended by a medical authority for the age group of the subject.

In some embodiments, the AD symptom is neurodegeneration. In some embodiments, the method results in treating, preventing, and/or delaying the progression and/or onset of neurodegeneration in the subject. In some embodiments, progression or onset of the neurodegeneration is slowed, halted, or reversed over a defined period of time following administration of the composition, as measured by a medically-recognized technique. In some embodiments, the neurodegeneration is positively impacted by the administered composition, as measured by a medically-recognized technique. In some embodiments, the progression or onset of the neurodegeneration and/or the positive impact on neurodegeneration is measured quantitatively or qualitatively by one or more techniques selected from electroencephalogram (EEG), neuroimaging, functional Mill, structural Mill, diffusion tensor imaging (DTI), [18F]fluorodeoxyglucose (FDG) PET, agents that label amyloid, [18F]F-dopa PET, radiotracer imaging, volumetric analysis of regional tissue loss, specific imaging markers of abnormal protein deposition, multimodal imaging, and biomarker analysis. In some embodiments, the progression or onset of neurodegeneration is slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique. In some embodiments, each defined period of time is independently selected from about 1 day to about 10 days, about 10 days to about 30 days, about 30 days to about 3 months, about 3 months to about 6 months, about 6 months to about 12 months, and about greater than 12 months.

There are provided, in some embodiments, kits comprising: a NK1R antagonist (e.g., aprepitant) or a pharmaceutically acceptable salt, solvate, stereoisomer, or prodrug thereof, and a label indicating that the kit is for preventing, delaying the onset of, or treating AD. There are provided, in some embodiments, compositions. comprising: a NK1R antagonist (e.g., aprepitant) or a pharmaceutically acceptable salt, solvate, stereoisomer, or prodrug thereof for use in treating AD. The composition can comprise: a NK1R antagonist (e.g., aprepitant) or a pharmaceutically acceptable salt, solvate, stereoisomer, or prodrug thereof for use in delaying or reducing the likelihood of onset of AD. The composition can comprise: a NK1R antagonist (e.g., aprepitant) or a pharmaceutically acceptable salt, solvate, stereoisomer, or prodrug thereof for use in treating, preventing, or reversing cognitive decline in clinical or pre-clinical AD. The composition can comprise: a NK1R antagonist (e.g., aprepitant) or a pharmaceutically acceptable salt, solvate, stereoisomer, or prodrug thereof for use in delaying or reversing the progression of AD. The AD can be, for example, early stage AD, mid-stage AD, and/or late-stage AD. In some embodiments, the AD is sporadic (non-hereditary) AD. In some embodiments, the AD is familial (hereditary) AD.

In some embodiments, the composition comprises fosaprepitant.

DETAILED DESCRIPTION

Figure 1:
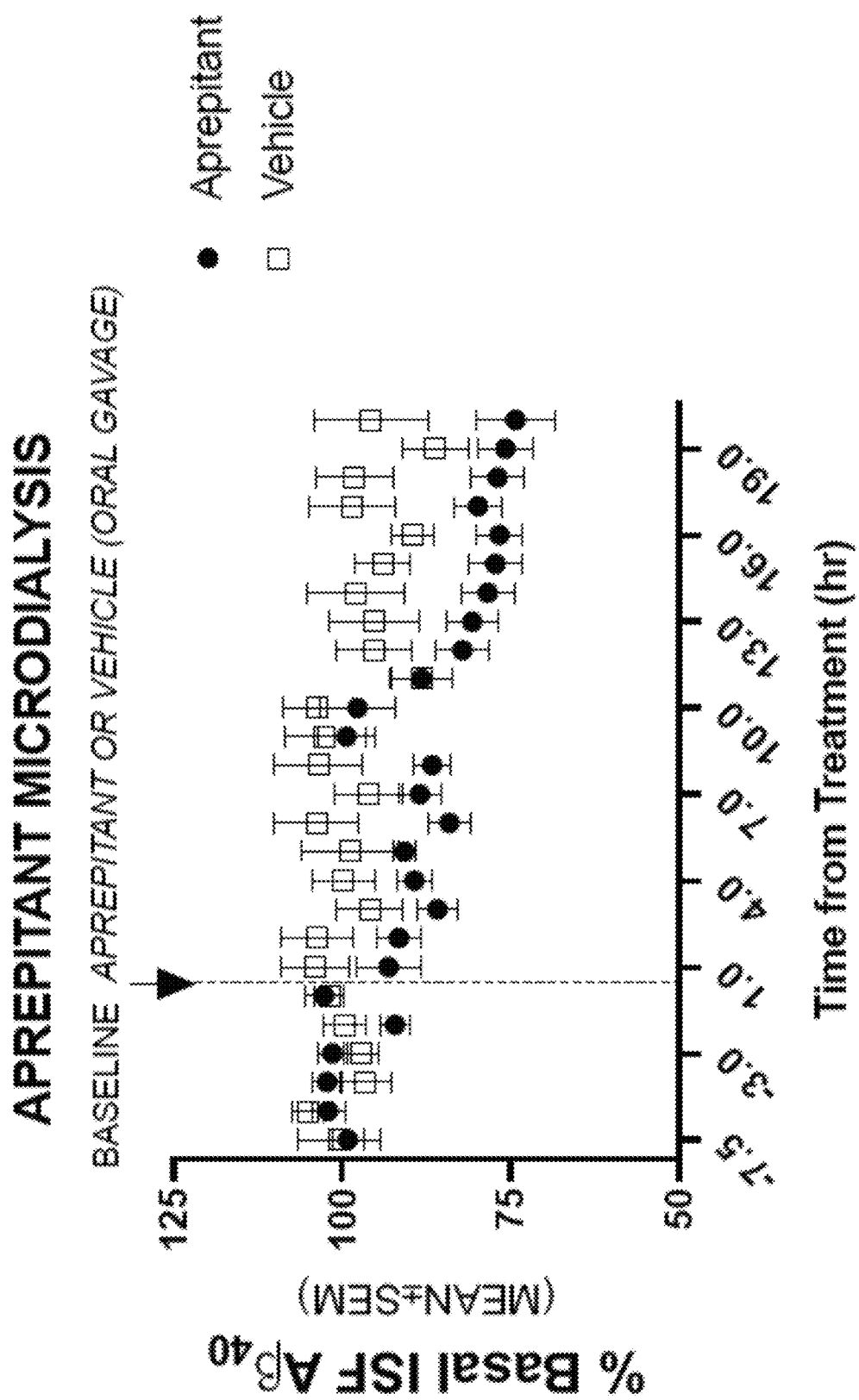
FIG. 1 depicts non-limiting exemplary microdialysis data from a study as described in Example 6 showing the brain interstitial fluid (ISF) Aβ levels in the aprepitant treated group compared to the vehicle treated group.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and other databases referred to herein are incorporated by reference in their entirety with respect to the related technology.

Disclosed herein include methods for treating Alzheimer's disease (AD). In some embodiments, the method comprises: administering to a subject in need thereof a composition comprising a NK1R antagonist (e.g., aprepitant) or a pharmaceutically acceptable salt, solvate, stereoisomer, or prodrug thereof.

Disclosed herein are methods for delaying or reducing the likelihood of onset of AD. In some embodiments, the method comprises: administering to a subject in need thereof a composition comprising a NK1R antagonist (e.g., aprepitant) or a pharmaceutically acceptable salt, solvate, stereoisomer, or prodrug thereof, thereby delaying or reducing the likelihood of onset of AD in the subject.

Disclosed herein are methods for treating, preventing, or reversing cognitive decline in clinical or pre-clinical AD. In some embodiments, the method comprises: administering to a subject in need thereof a composition comprising a NK1R antagonist (e.g., aprepitant) or a pharmaceutically acceptable salt, solvate, stereoisomer, or prodrug thereof.

Disclosed herein are methods for delaying or reversing the progression of AD. In some embodiments, the method comprises: administering to a subject in need thereof a composition comprising a NK1R antagonist (e.g., aprepitant) or a pharmaceutically acceptable salt, solvate, stereoisomer, or prodrug thereof.

There are provided, in some embodiments, kits. The kit can comprise: a NK1R antagonist (e.g., aprepitant) or a pharmaceutically acceptable salt, solvate, stereoisomer, or prodrug thereof, and a label indicating that the kit is for preventing, delaying the onset of, or treating AD.

There are provided, in some embodiments, compositions. The composition can comprise: a NK1R antagonist (e.g., aprepitant) or a pharmaceutically acceptable salt, solvate, stereoisomer, or prodrug thereof for use in treating AD. The composition can comprise: a NK1R antagonist (e.g., aprepitant) or a pharmaceutically acceptable salt, solvate, stereoisomer, or prodrug thereof for use in delaying or reducing the likelihood of onset of AD. The composition can comprise: a NK1R antagonist (e.g., aprepitant) or a pharmaceutically acceptable salt, solvate, stereoisomer, or prodrug thereof for use in treating, preventing, or reversing cognitive decline in clinical or pre-clinical AD. The composition can comprise: a NK1R antagonist (e.g., aprepitant) or a pharmaceutically acceptable salt, solvate, stereoisomer, or prodrug thereof for use in delaying or reversing the progression of AD.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, a "subject" refers to an animal that is the object of treatment, observation or experiment. "Animals" include cold- and warm-blooded vertebrates and invertebrates such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional, such as a Medical Doctor (i.e. Doctor of Allopathic medicine or Doctor of Osteopathic medicine) or a Doctor of Veterinary Medicine, to attempt to cure, or at least ameliorate the effects of, a particular disease or disorder or to prevent the disease or disorder from occurring in the first place.

As used herein, "administration" or "administering" refers to a method of giving a dosage of a pharmaceutically active ingredient to a subject.

As used herein, a "dosage" refers to the combined amount of the active ingredient (e.g., NK1R antagonist).

As used herein, a "unit dosage" refers to an amount of therapeutic agent administered to a patient in a single dose.

As used herein, a "daily dosage" refers to the total amount of therapeutic agent administered to a patient in a day.

As used herein, "therapeutic agent" or "pharmaceutically active ingredient" refers to a compound, which is suitable for or useful in preventing, modifying disease pathogenesis in a beneficial way, or treating a disease. As used herein, "therapeutically effective amount" or "pharmaceutically effective amount" refers to an amount of a therapeutic agent, which has a therapeutic effect. For example, in some embodiments, a therapeutically effective amount means an amount of therapeutic agent which produces the desired therapeutic effect as judged by clinical trial results and/or model animal studies. As used herein, the term "prophylactically effective amount" means an amount of a therapeutic agent which produces a prophylactic effect.

As used herein, a "therapeutic effect" relieves, to some extent, one or more of the symptoms of a disease or disorder. For example, in some embodiments, a therapeutic effect may be measured by one or more medically-recognized techniques. In some embodiments, a therapeutic effect may be observed by a reduction of the subjective discomfort that is communicated by a subject (e.g., reduced discomfort noted in self-administered patient questionnaire).

As used herein, "treat," "treatment," or "treating" refers to administering a therapeutic agent or pharmaceutical composition to a subject for prophylactic and/or therapeutic purposes. "Treat", "treatment", or "treating", as used herein, include alleviating or abrogating a disease or condition, or one or more symptoms associated with the disorder or condition, or alleviating or eradicating a cause(s) of the disorder or condition. As used herein, the term "prevent" or "preventing" refers to reducing or eliminating the onset of symptoms or complications of a disease or condition.

The term "therapeutic treatment" refers to administering treatment to a subject already suffering from a disease or condition. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition or symptoms associated with the disease or condition.

Methods of Treating and Preventing Alzheimer's Disease

Aprepitant is a highly selective antagonist of the G-protein coupled neurokinin-1 receptor. The neurokinin 1 receptor (NK1R) is a member of the tachykinin receptor family that preferentially binds the tachykinin substance P (SP) (Ubaldi et al. "Emerging targets for addiction neuropharmacology: from mechanisms to therapeutics." Progress in brain research. Vol. 224. Elsevier, 2016. 251-284; incorporated herein by reference in its entirety). The NK1 receptor is widely distributed in the central and peripheral nervous systems of mammals (e.g., spinal cord, medulla oblongata, striatum, hippocampus, and cerebral cortex) (Munoz and Coveñas "Substance P." (2018): 571-578; incorporated herein by reference in its entirety). In peripheral tissues, NK1 receptors are present on human pulmonary arterial blood vessels, on circular and longitudinal smooth muscle throughout the human gastrointestinal tract, and over ganglia of the myenteric plexus (Munoz & Coveñas). These receptors have been also located in the placenta, thyroid gland, endothelial cells, immune cells (e.g., dendritic cells, macrophages, monocytes, and lymphocytes) and in platelets (Muñoz & Coveñas). The occurrence of NK1 receptors in spleen, in thymus, on arterioles and venules of the lymph nodes, and on T lymphocytes provides further evidence for an involvement of SP in immunoregulation (Muñoz & Coveñas). The potent vasodilator action of SP is mediated primarily by binding to NK1 receptors on the endothelium of peripheral arterial blood vessels (Muñoz & Coveñas).

Substance P (SP) receptors are present in thymocytes, B and T lymphocytes, macrophages, mast cells, and astrocytes (Berczi et al. "Neuropeptides in Immunoregulation." Insights to Neuroimmune Biology. Elsevier, 2016. 133-181; incorporated herein by reference in its entirety). SP is a major mediator of neurogenic inflammation and capable of inducing mast cell degranulation, plasma extravasation, and bronchoconstriction (Berczi et al.). SP acts on lymphocytes, macrophages, and neutrophils (Berczi et al.). Lymphocyte proliferation and lymphokine production are enhanced by SP, whereas the effect on immunoglobulin secretion is variable (Berczi et al.). SP increased Fcγ and receptors, decreased C3b on eosinophils, released TNF-α from macrophages, and modified macrophage function during stress (Berczi et al.).

The glycosylation/phosphorylation of the NK1 receptor influences the NK1 receptor signaling (Muñoz & Coveñas). SP generates second messengers and affects many signaling pathways controlling the cell function: activation of phospholipases A2/C, protein kinases A/C and adenylyl cyclase, synthesis of diacylglicerol/inositol triphosphate/arachidonic acid, mobilization of intracellular $Ca^{2+}$ generation of thromboxane/leukotrienes, phosphorylation of myosin regulatory light chain, and activation of Rho-associated protein-kinase (ROCK) (Muñoz & Coverias). SP, via the NK1 receptor, transactivates the epidermal growth factor receptor (EGFR) leading to the activation of mitogen-activated protein kinases (MAPK), extracellular signal-regulated kinases (ERK) 1 and 2, DNA synthesis and proliferation (Muñoz & Coverias). SP exerts an antiapoptotic effect involving the Janus kinase 2 (JAK-2) and phosphoinositide 3-kinase (PI3K)-mediated activation of the antiapoptotic molecule Akt (protein kinase B) (Muñoz & Coveñas). SP activates p38, promotes the synthesis of proinflammatory cytokines (e.g., interleukin-6, interleukin-8) and activates proinflammatory transcription factors (e.g., nuclear factor kappa B (NF-κB) by mechanisms in which the activation of the Rho family kinases is involved) (Muñoz & Coveñas).

There are provided, in some embodiments, methods and compositions for treating Alzheimer's disease (AD). In some embodiments, the method comprises: administering to a subject in need thereof a composition comprising an NK1R antagonist (e.g., aprepitant) or a pharmaceutically acceptable salt, solvate, stereoisomer, or prodrug thereof. Disclosed herein are methods and compositions for delaying or reducing the likelihood of onset of AD. In some embodiments, the method comprises: administering to a subject in need thereof a composition comprising a NK1R antagonist (e.g., aprepitant) or a pharmaceutically acceptable salt, solvate, stereoisomer, or prodrug thereof, thereby delaying or reducing the likelihood of onset of AD in the subject.

There are provided, in some embodiments, methods and compositions for treating, preventing, or reversing cognitive decline in clinical or pre-clinical AD. In some embodiments, the method comprises: administering to a subject in need thereof a composition comprising a NK1R antagonist (e.g., aprepitant) or a pharmaceutically acceptable salt, solvate, stereoisomer thereof. Disclosed herein include methods and compositions for delaying or reversing the progression of AD. In some embodiments, the method comprises: administering to a subject in need thereof a composition comprising a NK1R antagonist (e.g., aprepitant) or a pharmaceutically acceptable salt, solvate, stereoisomer, or prodrug thereof.

In some embodiments, the composition comprises a therapeutically or prophylactically effective amount of a NK1R antagonist (e.g., aprepitant) or a pharmaceutically acceptable salt, solvate, stereoisomer, or prodrug thereof. In some embodiments, the subject is a mammal. In some embodiments, the subject is a human. In some embodiments, said subject is a human over 40 years old, over 50 years old, over 60 years old, over 70 years old, over 80 years old, and/or over 85 years old. In some embodiments, the subject in need thereof has AD, is suspected of having AD, or is at a risk of having AD. In some embodiments, said subject is diagnosed with mild cognitive impairment potentially related to AD, early stage AD, mid-stage AD, or late-stage AD. In some embodiments, said AD is sporadic (non-hereditary) AD. In some embodiments, said AD is familial (hereditary) AD. Diagnosis of different types of AD and one or more symptoms associated with AD can be conducted by methods and techniques known in the art. For example, diagnosis of mild cognitive impairment due to Alzheimer's disease can be performed as described in Alert et al. Alzheimers Dement. 2011 May ; 7(3): 270-279. doi:10.1016/j.jalz.2011.03.008, the content of which is incorporated herein by reference in its entirety. The diagnosis of mild cognitive impairment due to Alzheimer's disease, in some embodiments, includes two sets of criteria: (1) core clinical criteria that could be used by healthcare providers without access to advanced imaging techniques or cerebrospinal fluid analysis, and (2) research criteria that could be used in clinical research settings, including clinical trials. The second set of criteria incorporate the use of biomarkers based on imaging and cerebrospinal fluid measures. The final set of criteria for mild cognitive impairment due to AD has four levels of certainty, depending on the presence and nature of the biomarker findings. In some embodiments, the methods and compositions disclosed herein are used to treat and relieve one or more symptoms related to AD, including mild cognitive impairment potentially related to AD. In some embodiments, the subject suffers from Mild Cognitive Impairment (MCI), for example subject suffering from MCI and has an abnormal brain positron emission tomography (PET) scan or spinal fluid test for amyloid beta protein, which is the protein in amyloid plaques (one of the two hallmarks of Alzheimer's). In some embodiments, the subject is a subject diagnosed of MCI due to Alzheimer's disease. In some embodiments, the methods and compositions disclosed herein are used to treat MCI.

There are provided, in some embodiments, methods of delaying or reducing the likelihood of onset of AD. In some embodiments, the method comprises: administering to a subject in need thereof a composition comprising a NK1R antagonist (e.g., aprepitant) or a pharmaceutically acceptable salt, solvate, stereoisomer, or prodrug thereof, thereby delaying or reducing the likelihood of onset of AD in the subject, wherein the subject in need thereof is a subject that is at a risk of suffering from AD. In some embodiments, AD is prevented from occurring. In some embodiments, the onset of AD is delayed. The delay can be, for example, days, weeks, months, or years. In some embodiments, the onset of AD is delayed by at least, or at least about, one, two, three, four, five, six, seven, eight, nine, ten, or more weeks. In some embodiments, the onset of AD is delayed by at least, or at least about, one, two, three, four, five, six, seven, eight, nine, ten, eleven, twelve, or more months. In some embodiments, the onset of AD is delayed by at least, or at least about, one, two, three, four, five, six, seven, eight, nine, ten, eleven, twelve, or more years. One or more methods described herein for detecting/diagnosing AD and one or more symptoms associated with AD can be used to determine the delay in the onset of AD.

Administration of an NK-1 receptor antagonist (e.g., aprepitant) or a pharmaceutically acceptable salt, solvate, stereoisomer, or prodrug thereof as disclosed herein reduces or prevents neurogenic inflammation in the brain in some embodiments. "Neurogenic inflammation," as used herein, shall be given its ordinary meaning, and includes the local release of inflammatory mediators from afferent neurons such as substance P and calcitonin gene-related peptide and/or their associated downstream effects. The terms "inflammation" and "inflammatory response" shall be given their ordinary meaning, and also include immune-related responses and/or allergic reactions to a physical, chemical, or biological stimulus. Measuring brain inflammation can comprise measuring the level of a pro-inflammatory cytokine, an anti-inflammatory cytokine, or a combination of pro-inflammatory cytokines and anti-inflammatory cytokines. Brain inflammation can comprise mast cell degranulation and plasma extravasation. Administering the composition can result in an at least, or at least about, 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, 150%, 200%, 250%, 500%, 1000%, or a range or a number between any two of these values) reduction of one or more of mast cell degranulation and plasma extravasation. In some embodiments of the methods and compositions provided herein, lymphopenia and/or mononuclear cell infiltration in the brain is reduced by at least, or at least about, 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, 150%, 200%, 250%, 500%, 1000%, or a range or a number between any two of these values).

Administering the composition comprising a NK1R antagonist (e.g., aprepitant) or a pharmaceutically acceptable salt, solvate, stereoisomer, or prodrug thereof can result in an at least, or at least about, 2% (e.g., at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 40%, at least about 50%, at least about 75%, at least about 100%, or a range or a number between any two of these values) reduction of one or more of (i) formation of plaques, (ii) amyloid fibril formation, (iii) amyloid-induced cellular toxicity or microglial activation, (iv) amyloid-induced neurotoxicity, (v) the rate or amount of amyloid aggregation, (vi) fibril formation, or deposition, (vii) the degree of amyloid deposition, (viii) amyloid-induced inflammation, (ix) neuroinflammation, (x) neurofibrillary tangles (NFTs, which are tangles containing hyperphosphorylated tau), and (xi) concentration of phosphorylated tau. Disclosed herein include a method for clinically assessing the effect of aprepitant, or a pharmaceutically acceptable salt, solvate, stereoisomer, or prodrug thereof, on tau neurofibrillary tangles and/or phosphorylated tau. In some embodiments, the methods disclosed herein include a step of assessing the subject need of treatment on tau neurofibrillary tangles and/or phosphorylated tau, and the step can be prior to, during, and after the treatment to the subject. In some embodiments, the methods and composition disclosed herein can reduce or slow down the formation of neurofibrillary tangles (i.e., tangles containing hyperphosphorylated tau). In some embodiments, the methods and composition disclosed herein can reduce the amount of neurofibrillary tangles or to reverse neurofibrillary tangle formation. In some embodiments, the methods and composition disclosed herein can reduce the concentration or the amount of phosphorylated tau.

In some embodiments, the reduction of neuroinflammation comprises changes in one or more of cell signaling molecule production, activation of glia or glial activation pathways and responses, proinflammatory cytokines or chemokines, oxidative stress-related responses, acute phase proteins, components of the complement cascade, protein kinase activity, cell damage and cell death signal transduction pathways.

The method can comprise measuring one or more AD symptom in the subject before administering the composition to the subject, after administering the composition to the subject, or both. In some embodiments, administering the composition treats, prevents, improves, and/or resolves one or more AD symptom. In some embodiments, administering the composition treats, prevents, improves, and/or resolves one or more AD symptom by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, or a range or a number between any two of these values. In some embodiments, the progression or onset of AD is slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or a range or a number between any two of these values. In some embodiments, the progression or onset of AD is evaluated by measuring one or more symptoms of AD. In some embodiments, the progression or onset of AD of is measured quantitatively or qualitatively by one or more techniques selected from the group comprising electroencephalogram (EEG), neuroimaging, functional MRI, structural MRI, diffusion tensor imaging (DTI), [18F] fluorodeoxyglucose (FDG) PET, agents that label amyloid, [18F]F-dopa PET, radiotracer imaging, volumetric analysis of regional tissue loss, specific imaging markers of abnormal protein deposition, multimodal imaging, biomarker analysis, or any combination thereof.

The AD symptom can be, for example, (a) a symptom from the Integrated Alzheimer's Disease Rating Scale (iADRS) selected from personal belonging management, selection of clothes, ability to dress self, ability to clean habitation, financial management ability, writing ability, ability to keep appointments, ability to use telephone, ability to prepare food for self, travel ability, awareness of current events, reading ability, interest in television, ability to shop for self, ability to remain alone, ability to perform chores, ability to perform a hobby or game, driving ability, self-management of medications, ability to initiate and finish complex tasks, and ability to initiate and finish simple tasks; (b) a symptom from the Alzheimer's Disease Assessment Scale-Cognitive subscale (ADAS-Cog) selected from learning, naming, command following, ideational praxis, constructional praxis, orientation, and recognition memory; (c) a symptom from the Alzheimer's Disease Cooperative Study-instrumental Activities of Daily Living (ADCS-iADL) wherein the symptom is any of the symptoms recited in (a) or (b); (d) constipation; (e) depression; (f) cognitive impairment; (g) short term memory impairment; (h) long term memory impairment; (i) concentration impairment; (j) coordination impairment; (k) mobility impairment; (l) speech impairment; (m) mental confusion; (n) sleep problem, sleep disorder, or sleep disturbance; (o) circadian rhythm dysfunction; (p) REM disturbed sleep; (q) REM behavior disorder; (r) hallucinations; (s) fatigue; (t) apathy; (u) erectile dysfunction; (v) mood swings; (w) urinary incontinence; (x) mild cognitive impairment; (y) neurodegeneration; or any combination thereof. In some embodiments, administering the composition comprising a NK1R antagonist (e.g., aprepitant) or a pharmaceutically acceptable salt, solvate, stereoisomer, or prodrug thereof results in an at least, or at least about, 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, 150%, 200%, 250%, 500%, 1000%, or a range or a number between any two of these values) reduction of one or more AD symptom of the subject as compared to that in the subject before administration of the composition.

The one or more AD symptom can comprise a sleep problem, sleep disorder, sleep disturbance, circadian rhythm dysfunction, REM disturbed sleep, or REM behavior disorder. In some embodiments, (a) the sleep disorder or sleep disturbance comprises a delay in sleep onset, sleep fragmentation, REM-behavior disorder, sleep-disordered breathing including snoring and apnea, day-time sleepiness, microsleep episodes, narcolepsy, hallucinations, or any combination thereof; (b) the REM-behavior disorder comprises vivid dreams, nightmares, and acting out the dreams by speaking or screaming, or fidgeting or thrashing of arms or legs during sleep; (c) the method results in a positive change in the sleeping pattern of the subject over a defined period of time; (d) the method results in a positive change in the sleeping pattern of the subject over a defined period of time, wherein the positive change is defined as: (i) an increase in the total amount of sleep obtained of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%; and/or (ii) a percent decrease in the number of awakenings during the night selected from about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or a range or a number between any two of these values; (e) as a result of the method the subject obtains the total number of hours of sleep recommended by a medical authority for the age group of the subject; and/or (e) each defined period of time is independently selected from about 1 day to about 10 days, about 10 days to about 30 days, about 30 days to about 3 months, about 3 months to about 6 months, about 6 months to about 12 months, and about greater than 12 months.

The one or more AD symptom can comprise a hallucination(s). In some embodiments, (a) the hallucination comprises a visual, auditory, tactile, gustatory or olfactory hallucination; (b) the method results in a decreased number of hallucinations over a defined period of time in the subject; (c) the method results in a decreased number of hallucinations over a defined period of time in the subject selected from by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%; (d) the method results in the subject being hallucination-free; (e) the method results in a decreased severity of hallucinations in the subject over a defined period of time, wherein the decrease in severity is measured by one or more medically-recognized techniques; (f) the method results in a decreased severity of hallucinations in the subject over a defined period of time, wherein the decrease in severity is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, or a range or a number between any two of these values, as measured by one or more medically recognized techniques; (g) the one or more medically recognized techniques is selected from Chicago Hallucination Assessment Tool (CHAT), The Psychotic Symptom Rating Scales (PSYRATS), Auditory Hallucinations Rating Scale (AHRS), Hamilton Program for Schizophrenia Voices Questionnaire (HPSVQ), Characteristics of Auditory Hallucinations Questionnaire (CAHQ), Mental Health Research Institute Unusual Perception Schedule (MUPS), positive and negative syndrome scale (PANSS), scale for the assessment of positive symptoms (SAPS), Launay-Slade hallucinations scale (LSHS), the Cardiff anomalous perceptions scale (CAPS), and structured interview for assessing perceptual anomalies (SIAPA); and/or (h) each defined period of time is independently selected from about 1 day to about 10 days, about 10 days to about 30 days, about 30 days to about 3 months, about 3 months to about 6 months, about 6 months to about 12 months, and about greater than 12 months.

The one or more AD symptom can comprise depression. In some embodiments, (a) the method results in improvement in the subject's depression over a defined period of time, as measured by one or more clinically-recognized depression rating scale; (b) the method results in improvement in the subject's depression over a defined period of time, as measured by one or more clinically-recognized depression rating scale and the improvement is in one or more depression characteristics selected from mood, behavior, bodily functions such as eating, sleeping, energy, and sexual activity, and/or episodes of sadness or apathy; (c) the method results in improvement in the subject's depression over a defined period of time, as measured by one or more clinically-recognized depression rating scale, and the improvement a subject experiences following treatment is about 5, about 10, about 15, about 20, about 25, about 30, about 35, about 40, about 45, about 50, about 55, about 60, about 65, about 70, about 75, about 80, about 85, about 90, about 95 or about 100%; and/or (d) each defined period of time is independently selected from about 1 day to about 10 days, about 10 days to about 30 days, about 30 days to about 3 months, about 3 months to about 6 months, about 6 months to about 12 months, and about greater than 12 months.

The one or more AD symptom can comprise cognitive impairment. In some embodiments, (a) progression or onset of the cognitive impairment is slowed, halted, or reversed over a defined period of time following administration of the composition, as measured by a medically-recognized technique; (b) the cognitive impairment is positively impacted by the administered composition, as measured by a medically-recognized technique; (c) the cognitive impairment is positively impacted by the administered composition, as measured by a medically-recognized technique and the positive impact on and/or progression of cognitive impairment is measured quantitatively or qualitatively by one or more techniques selected from Mini-Mental State Exam (MMSE), Mini-cog test, and a computerized test selected from Cantab Mobile, Cognigram, Cognivue, Cognision, or Automated Neuropsychological Assessment Metrics; (d) the progression or onset of cognitive impairment is slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique; and/or (e) each defined period of time is independently selected from about 1 day to about 10 days, about 10 days to about 30 days, about 30 days to about 3 months, about 3 months to about 6 months, about 6 months to about 12 months, and about greater than 12 months.

The one or more AD symptom can comprise constipation. In some embodiments, (a) the composition causes the subject to have a bowel movement; and/or (b) the method results in an increase in the frequency of bowel movement in the subject; and/or (c) the method results in an increase in the frequency of bowel movement in the subject and the increase in the frequency of bowel movement is defined as: (i) an increase in the number of bowel movements per week of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%; and/or (ii) a percent decrease in the amount of time between each successive bowel movement selected from about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%; and/or (d) as a result of the method the subject has the frequency of bowel movement recommended by a medical authority for the age group of the subject.

The one or more AD symptom can comprise neurodegeneration. In some embodiments, (a) the method results in treating, preventing, and/or delaying the progression and/or onset of neurodegeneration in the subject; (b) progression or onset of the neurodegeneration is slowed, halted, or reversed over a defined period of time following administration of the composition, as measured by a medically-recognized technique; (c) the neurodegeneration is positively impacted by the administered composition, as measured by a medically-recognized technique; (d) the progression of (b) and/or the positive impact of (c) is measured quantitatively or qualitatively by one or more techniques selected from electroencephalogram (EEG), neuroimaging, functional MM, structural MM, diffusion tensor imaging (DTI), [18F] fluorodeoxyglucose (FDG) PET, agents that label amyloid, [18F]F-dopa PET, radiotracer imaging, volumetric analysis of regional tissue loss, specific imaging markers of abnormal protein deposition, multimodal imaging, and biomarker analysis; (e) the progression or onset of (b) is slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique; and/or (f) each defined period of time is independently selected from about 1 day to about 10 days, about 10 days to about 30 days, about 30 days to about 3 months, about 3 months to about 6 months, about 6 months to about 12 months, and about greater than 12 months.

Therapeutic Agents

The NK1R antagonist can be or can include a selective NK1R antagonist. Non-limiting examples of NK1R antagonists include aprepitant (L-754030 or MK-(0)869), fosaprepitant (L-758298), befetupitant, casopitant (GW-679769), dapitant (RPR-100893), ezlopitant (CJ-11974), lanepitant (LY-303870), maropitant (CJ-11972), netupitant, nolpitantium (SR-140333), orvepitant (GW-823296), rolapitant (SCH-619734), SCH-720881 (active metabolite of rolapitant), serlopitant (MK-(0)594 or VPD-737), tradipitant (VLY-686 or LY-686017), vestipitant (GW-597599), vofopitant (GR-205171), hydroxyphenyl propamidobenzoic acid, maltooligosaccharides (e.g., maltotetraose and maltopentaose), spantides (e.g., spantide I and II), AV-608, AV-818, AZD-2624, BIIF 1149 CL, CGP-49823, CJ-17493, CP-96345, CP-99994, CP- 122721, DNK-333, FK-224, FK-888, GR-82334, GR-205171, GSK-424887, HSP-117, KRP-103, L-703606, L-733060, L-736281, L-759274, L-760735, LY-686017, M516102, MDL-105212, MK-0303 (L-001182885), MK- 8478 (L-001983867), NKP-608, R-1 16031, R-1 16301, RP-67580, S-41744, SCH-206272, SCH-388714, SCH-900978, SLV-317, SSR-240600, T-2328, TA-5538, TAK-637, TKA-731, WIN-51708, ZD-4974, ZD-6021, cycloalkyl (including, but not limited to, cyclopentyl, cyclohexyl and cycloheptyl) tachykinin receptor antagonists disclosed in U.S. Pat. No. 5,750,549, hydroxymethyl ether hydroisoindoline tachykinin receptor antagonists disclosed in U.S. Pat. No. 8,124,633, and analogs, derivatives, prodrugs, metabolites and salts thereof. Non-limiting examples of NK1R antagonists also include Casopitant, CGP49823, CP-122,721, CP-96,345, CP-99,994, FK 888, GR 82334, GR 94800, GR203040, GR-205171, GSK1144814, GSK206136, GSK424887, GW679769, HSP-117, L 703,606, L 732,138, L 733,060, L 742,694, L668,169, LY 303241, LY 303870, LY 306740, Maropitant, MEN 11149, Orvepitant, PD 154075, R-544, RP-67580, RPR 100893, SCH619734, Spantide II, Spantide III, Spendide, SR140333, Vestipitant, WIN-41,708, WIN-62,577, and analogs, derivatives, prodrugs, metabolites and salts thereof. Non-limiting examples of NK1R antagonists also include FK 888(Fujisawa); GR 205171 (Glaxo Wellcome); LY 303870 (Lilly); MK 869 (Merck); GR82334 (Glaxo Wellcome); L758298 (Merck); L 733060 (Merck); L 741671 (Merck); L 742694 (Merck); PD 154075 (Parke-Davis); Si 8523 (Servier); Si 9752 (Servier); OT 7100 (Otsuka); WIN 51708 (Sterling Winthrop); NKP-608A; TKA457; DNK333; CP-96345; CP-99994; CP122721; L-733060; L-741671; L742694; L-758298; L-754030; GR-203040; GR-205171; RP-67580; RPR-100893 (dapitant); RPR-107880; RPR-111905; FK-888; SDZ-NKT-343; MEN-10930; MEN-11149; 5-18523; S-19752; PD-154075 (CAM-4261); SR-140333; LY-303870 (lanepitant); EP-00652218; EP00585913; L-737488; CGP-49823; WIN-51708; SR-48968 (saredutant); SR-144190; YM383336; ZD-7944; MEN-10627; GR-159897; RPR-106145; PD-147714 (CAM-2291); ZM253270; FK-224; MDL-1 05212A; MDL-105172A; L-743986; L-743986 analogs; S-16474; SR-1 42801 (osanetant); PD-161182; SB-223412; SB-222200; and analogs, derivatives, prodrugs, metabolites and salts thereof. In some embodiments, the NK1R antagonist is or comprises: aprepitant or fosaprepitant as shown below:

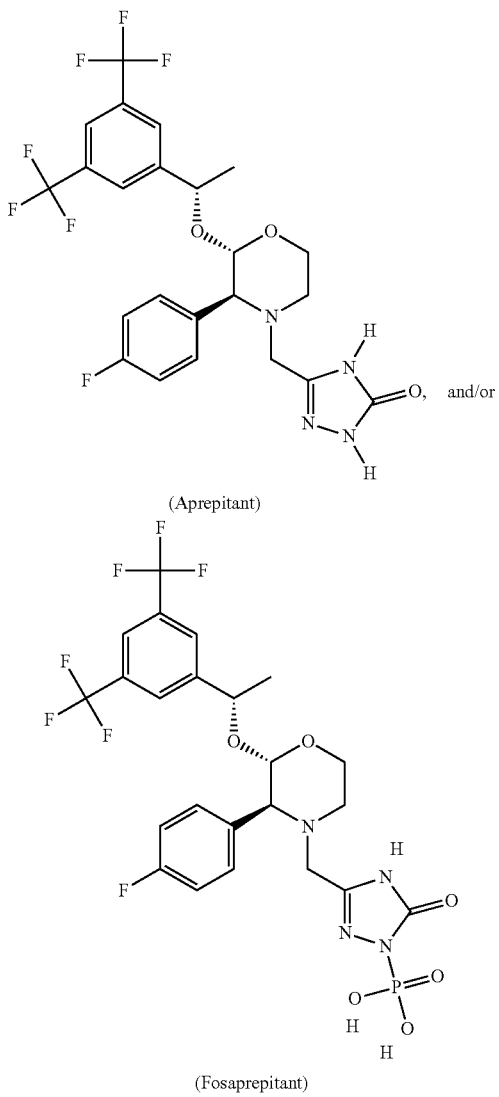

(Aprepitant)

(Fosaprepitant)

In some embodiments, the methods of the disclosure comprise administering to the subject in need thereof a NK1R antagonist (e.g., aprepitant) or a pharmaceutically acceptable salt, solvate, stereoisomer, or prodrug thereof as the sole therapeutic agent. In some embodiments, the methods of the disclosure comprise administering to the subject in need thereof a composition comprising a NK1R antagonist (e.g., aprepitant) or a pharmaceutically acceptable salt, solvate, stereoisomer, or prodrug thereof, wherein no additional therapeutic agents (e.g., anti-AD agents) are co-administered for the treatment of Alzheimer's disease. In some embodiments, the methods of the disclosure comprise administering to the subject in need thereof a composition comprising a NK1R antagonist (e.g., aprepitant) or a pharmaceutically acceptable salt, solvate, stereoisomer, or prodrug thereof, wherein no additional therapeutic agents (e.g., anti-AD agents) are co-administered for the treatment of Alzheimer's disease during the pendency of the treatment with aprepitant.

In some embodiments, the method of treating Alzheimer's disease (AD), comprises administering to a subject in need thereof a composition comprising aprepitant or a pharmaceutically acceptable salt, solvate, stereoisomer, or prodrug thereof as the sole therapeutic agent, thereby treating AD in the subject. In some embodiments, a method of delaying or reducing the likelihood of onset of Alzheimer's disease (AD), comprises administering to a subject in need thereof a composition comprising aprepitant or a pharmaceutically acceptable salt, solvate, stereoisomer, or prodrug thereof as the sole therapeutic agent, thereby delaying or reducing the likelihood of onset of AD in the subject. In some embodiments, a method of treating, preventing, or reversing cognitive decline in clinical or pre-clinical Alzheimer's disease (AD), comprises administering to a subject in need thereof a composition comprising aprepitant or a pharmaceutically acceptable salt, solvate, stereoisomer, or prodrug thereof as the sole therapeutic agent, thereby treating, preventing, or reversing cognitive decline in clinical or pre-clinical AD in the subject. In some embodiments, a method of delaying or reversing the progression of Alzheimer's disease (AD), comprising administering to a subject in need thereof a composition comprising aprepitant or a pharmaceutically acceptable salt, solvate, stereoisomer, or prodrug thereof as the sole therapeutic agent, thereby delaying or reversing the progression of AD in the subject.

In some embodiments, a NK1R antagonist (e.g., aprepitant) or a pharmaceutically acceptable salt, solvate, stereoisomer, or prodrug thereof is therapeutically effective as the sole therapeutic agent for the treatment of Alzheimer's disease. In some embodiments, a NK1R antagonist (e.g., aprepitant) or a pharmaceutically acceptable salt, solvate, stereoisomer, or prodrug thereof is prophylactically effective as the sole therapeutic agent for the treatment of Alzheimer's disease. In some embodiments, a NK1R antagonist (e.g., aprepitant) or a pharmaceutically acceptable salt, solvate, stereoisomer, or prodrug thereof is therapeutically effective and/or prophylactically effective for the treatment of Alzheimer's disease regardless of whether any additional therapeutic agent is co-administered. Aprepitant or fosaprepitant is the only therapeutically or prophylactically effective agent in the methods and compositions disclosed herein, in some embodiments. In some embodiments, the method does not comprise administrating any other therapeutically effective agent for treating AD.

In some embodiments, the method can comprise administering to the subject in need thereof one or more additional therapeutic agents (e.g., anti-AD agents). In some embodiments, the additional therapeutic agents (e.g., anti-AD agents) can be co-administered to the subject with the composition comprising the NK1R antagonist (e.g., aprepitant). In some embodiments, the additional therapeutic agents (e.g., anti-AD agents) can be administered to the subject before the administration of the composition comprising the NK1R antagonist (e.g., aprepitant), concomitantly with the administration of the composition comprising the NK1R antagonist (e.g., aprepitant), after the administration of the composition comprising the NK1R antagonist (e.g., aprepitant), or both. In some embodiments, the composition comprising the NK1R antagonist (e.g., aprepitant) can further comprise one or more additional therapeutic agents (e.g., anti-AD agents). In some embodiments, the one or more additional therapeutic agents (e.g., anti-AD agents) can include one or more of the following:

(i) acetylcholinesterase inhibitors, such as donepezil hydrochloride (ARICEPT, MEMAC), physostigmine salicylate (ANTILIRIUM), physostigmine sulfate (ESERINE), metrifonate, neostigmine, ganstigmine, pyridostigmine (MESTINON), ambenonium (MYTELASE), demarcarium, Debio 9902 (also known as ZT-1; Debiopharm), rivastigmine (EXELON), ladostigil, NP-0361, galantamine hydrobromide (RAZADYNE, RIMINYL, NIVALIN), tacrine (COGNEX), tolserine, velnacrine maleate, memoquin, huperzine A (HUP-A; NeuroHitech), phenserine, edrophonium (ENLON, TENSILON), and INM-176;

(ii) amyloid-β (or fragments thereof), such as A1-15 conjugated to pan HLA DR-binding epitope (PADRE), ACC-001 (Elan/Wyeth), ACI-01, ACI-24, AN-1792, Affitope AD-01, CAD106, and V-950;

(iii) antibodies to amyloid-β (or fragments thereof), such as ponezumab, solanezumab, bapineuzumab (also known as AAB-001), AAB-002 (Wyeth/Elan), ACI-01-Ab7, BAN-2401, intravenous Ig (GAMMAGARD), LY2062430 (humanized m266; Lilly), R1450 (Roche), ACU-5A5, huC091, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and EP1257584, and in U.S. Pat. No. 5,750,349;

(iv) amyloid-lowering or -inhibiting agents (including those that reduce amyloid production, accumulation and fibrillization) such as dimebon, davunetide, eprodisate, leuprolide, SK-PC-B70M, celecoxib, lovastatin, anapsos, oxiracetam, pramiracetam, varenicline, nicergoline, colostrinin, bisnorcymserine (also known as BNC), NICS-15 (Humanetics), E-2012 (Eisai), pioglitazone, clioquinol (also known as PBT1), PBT2 (Prana Biotechnology), flurbiprofen (ANSAID, FROBEN) and its R-enantiomertarenflurbil (FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), ARC031 (Archer Pharmaceuticals), CAD-106 (Cytos), LY450139 (Lilly), insulin-degrading enzyme (also known as insulysin), the gingko biloba extract EGb-761 (ROKAN, TEBONIN), tramiprosate (CEREBRIL, ALZHEMED), eprodisate (FIBRILLEX, KIACTA), compound W [3,5-bis(4-nitrophenoxy)benzoic acid], NGX-96992, neprilysin (also known as neutral endopeptidase (NEP)), scyllo-inositol (also known as scyllitol), atorvastatin (LIPITOR), simvastatin (ZOCOR), KLVFF-(EEX)3, SKF-74652, ibutamoren mesylate, BACE inhibitors such as ASP-1702, SCH-745966, JNJ-715754, AMG-0683, AZ-12304146, BMS-782450, GSK-188909, NB-533, E2609 and TTP-854; gamma secretase modulators such as ELND-007; and RAGE (receptor for advanced glycation end-products) inhibitors, such as TTP488 (Transtech) and TTP4000 (Transtech), and those disclosed in U.S. Pat. No. 7,285,293, including PTI-777;

(v) alpha-adrenergic receptor agonists, such as guanfacine (INTUNIV, TENEX), clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenytoin sodium (PHENYTEK), fosphenytoin (CEREBYX, PRODILANTIN), divalproex sodium (DEPAKOTE), gabapentin (NEURONTIN), pregabalin (LYRICA), topirimate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (LATUDA, also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine (SAPHRIS), Ioxapine (LOXITANE), molindone (MOBAN), perphenazine, thioridazine, thiothixine, trifluoperazine (STELAZINE), ramelteon, clozapine (CLOZARIL), norclozapine (ACP-104), risperidone (RISPERDAL), paliperidone (INVEGA), melperone, olanzapine (ZYPREXA), quetiapine (SEROQUEL), talnetant, amisulpride, ziprasidone (GEODON), blonanserin (LONASEN), and ACP-103 (Acadia Pharmaceuticals);

(x) calcium channel blockers such as omerizine, ziconotide, nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as nitecapone, tolcapone (TASMAR), entacapone (COMTAN), and tropolone;

(xii) central nervous system stimulants, such as atomoxetine, reboxetine, yohimbine, caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g., ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), predisolone acetate (OMNIPRED, PRED MILD, PRED FORTE), prednisolone sodium phosphate (ORAPRED ODT), methylprednisolone (MEDROL); methylprednisolone acetate (DEPO-MEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocryptine, fenoldopam (CORLOPAM), lisuride (DOPERGIN), terguride spergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), cariprazine, pardoprunox and sarizotan;

(xv) dopamine receptor antagonists, such as chlorpromazine, fluphenazine, haloperidol, loxapine, risperidone, thioridazine, thiothixene, trifluoperazine, tetrabenazine (NITOMAN, XENAZINE), 7-hydroxyamoxapine, droperidol (INAPSINE, DRIDOL, DROPLETAN), domperidone (MOTILIUM), L-741742, L-745870, raclopride, SB-277011A, SCH-23390, ecopipam, SKF-83566, and metoclopramide (REGLAN);

(xvi) dopamine reuptake inhibitors such as bupropion, safinamide, nomifensine maleate (MERITAL), vanoxerine (also known as GBR-12909) and its decanoate ester DBL-583, and amineptine;

(xvii) gamma-amino-butyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan, tiprolisant, S-38093, irdabisant, pitolisant, GSK-239512, GSK-207040, JNJ-5207852, JNJ-17216498, HPP-404, SAR-110894, trans-N-ethyl-3-fluoro-3-[3-fluoro-4-(pyrrol i di n-1-yl m ethyl)phenyl]-cyclobutanecarboxamide (PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-IL-12 antibody; Abbott), rituximab (RITUXAN), alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURINETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-(benzyloxy)-5-[(5-undecyl-2H-pyrrol-2-ylidene)methyl]-1H,1 'H-2,2'-bipyrrole (also known as PNU-156804);

(xxi) interferons, including interferon beta-1a (AVONEX, REBIF) and interferon beta-1b (BETA SERON, BETAFERON);

(xxii) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), LY-233536 and LY-235959 (both Lilly), methadone, (DOLOPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERESOTAT), gavestinel, and remacimide;

(xxiv) monoamine oxidase (MAO) inhibitors, such as selegiline (EMSAM), selegiline hydrochloride (I-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as cevimeline, levetiracetam, bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzensulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as bosutinib, condoliase, airmoclomol, lamotrigine, perampanel, aniracetam, minaprime, riluzole, N-hydroxy-1,2,4,9-tetrahydro-3H-carbazol-3-imine, desmoteplase, anatibant, astaxanthin, neuropeptide NAP (e.g., AL-108 and AL-208; both Allon Therapeutics), neurostrol, perampenel, ispronicline, bis(4-β-D-glucopyranosyloxybenzyl)-2-β-D-glucopyranosyl-2-isobutyltartrate (also known as dactylorhin B or DHB), formobactin, xaliproden (XAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADICUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-B-hydroxyepiandrosterone; Newron Pharmaceuticals), HF-0420 (also known as oligotropin), pyridoxal 5'-phosphate (also known as MC-1), microplasmin, S-18986, piclozotan, NP031112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUN-N8075 (Daiichi Suntory Biomedical Research), and zonampanel;

(xxvii) nicotinic receptor agonists, such as epibatidine, bupropion, CP-601927, varenicline, ABT-089 (Abbott), ABT-594, AZD-0328 (AstraZeneca), EVP-6124, R3487 (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxix) phosphodiesterase (PDE) inhibitors, including but not limited to, (a) PDE1 inhibitors (e.g., vinpocetine (CAVINTON, CERACTIN, INTELECTOL) and those disclosed in U.S. Pat. No. 6,235,742, (b) PDE2 inhibitors (e.g., erythro-9-(2-hydroxy-3-nonyl)adenine (EHNA), BAY 60-7550, and those described in U.S. Pat. No. 6,174,884), (c) PDE3 inhibitors (e.g., anagrelide, cilostazol, milrinone, olprinone, parogrelil, and pimobendan), (d) PDE4 inhibitors (e.g., apremilast, ibudilastroflumilast, rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (e) PDE5 inhibitors (e.g., sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, iodenafil, mirodenafil, DA-8159, and those disclosed in International Patent Applications WO2002/020521, WO2005/049616, WO2006/120552, WO2006/126081, WO2006/126082, WO2006/126083, and WO2007/122466), (f) PDE7 inhibitors; (g) PDE8 inhibitors; (h) PDE9 inhibitors (e.g., BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), (i) PDE10 inhibitors such as 2-({4-[1-methyl-4-(pyridin-4-yl)-1H-pyrazol-3-yl]phenoxy}methyl)quinolin-3(4H)-one and SCH-1518291; and (j) PDE11 inhibitors;

(xxx) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE);

(xxxi) β-secretase inhibitors, such as ASP-1702, SCH-745966, JNJ-715754, AMG-0683, AZ-12304146, BMS-782450, GSK-188909, NB-533, LY-2886721, E-2609, HPP-854, (+)-phenserine tartrate (POSIPHEN), LSN-2434074 (also known as LY-2434074), KMI-574, SCH-745966, Ac-rER ($N^2$-acetyl-D-arginyl-L-arginine), Ioxistatin (also known as E64d), and CA074Me;

(xxxii) γ-secretase inhibitors and modulators, such as BMS-708163 (Avagacest), WO20060430064 (Merck), DSP8658 (Dainippon), ITI-009, L-685458 (Merck), ELAN-G, ELAN-Z, 4-chloro-N-[(2S)-3-ethyl-1-hydroxypentan-2-yl]benzenesulfonamide;

(xxxiii) serotonin (5-hydroxytryptamine) 1A (5-$HT_{1A}$) receptor antagonists, such as spiperone, levo-pindolol, BMY 7378, NAD-299, S-(–)-UH-301, NAN 190, lecozotan;

(xxxiv) serotonin (5-hydroxytryptamine) 2C (5-$HT_{2c}$) receptor agonists, such as vabicaserin and zicronapine;

(xxxv) serotonin (5-hydroxytryptamine) 4 (5-HT4) receptor agonists, such as PRX-03140 (Epix);

(xxxvi) serotonin (5-hydroxytryptamine) 6 (5-HT6) receptor antagonists, such as A-964324, AVI-101, AVN-211, mianserin (TORVOL, BOLVIDON, NORVAL), methiothepin (also known as metitepine), ritanserin, ALX-1161, ALX-1175, MS-245, LY-483518 (also known as SGS518; Lilly), MS-245, Ro 04-6790, Ro 43-68544, Ro 63-0563, Ro 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix);

(xxxvii) serotonin (5-HT) reuptake inhibitors such as alaproclate, citalopram (CELEXA, CIPRAIVIIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine, neuralstem and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN);

(xxxix) Glycine transporter-1 inhibitors such as paliflutine, ORG-25935, JNJ-17305600, and ORG-26041;

(xl) AMPA-type glutamate receptor modulators such as perampanel, mibampator, selurampanel, GSK-729327, N-{(3S,4S)-4-[4-(5-cyanothiophen-2-yl)phenoxy]tetrahydro-furan-3-yl}propane-2-sulfonamide, and the like;

(xli) Janus kinase inhibitors (JAK) such as, but not limited to, tofacitinib, ruxolitinib, baricitinib, CYT387, GLPG0634, lestaurtinib, pacritinib, and TG101348; and/or (xlii) Interleukin-1 receptor-associated kinase 4 inhibitors (IRAK4) such as, but not limited to, PF-06650833.

The additional therapeutic agents provided herein can include a passive immunotherapy against amyloid beta or tau, or an inhibitor of acetylcholinestarase. In some embodiments, the therapeutic agent may be selected from one or more of:, CAD106, Gantenerumab, Crenezumab, IVIG, AADvad , ACI-35, NICS-15, CHF-5074, MK- 8931 , AZD 3293, LY33 14814, Elenbecestat, Tideglusib, Intranasal Humulin R, Intransal glulisine, SB742457 with donepezil, Azeliragon, Nivaldipine. See Godyn et al., Pharmacological Reports, 68:127-138, 2016. In some embodiments, the therapeutic agent may be selected from:, Aducanumab, ALZT-OP1 a+ALZT-OP1 b, Aripiprazole, AVP-786, AZD3293 (LY3314814), Brexprprazole (OPC-34712), CAD106, CNP520, Elenbecestat, Insulin (humulin), Lumateperone, JNJ-5486191 1 , Methylphenidate, MK-4305 (suvorexant), Nabilone, Nilvadipine, Pioglitazone, RVT- 101 (intepirdine), Sodium Oligo-mannurarate (GV-971), TRx0237, TTp488 (azeliragon), AADvad , ABBV-8E12, AD-SVF cells, ANAVEX 2-73, Atomoxetine, AVP-786, AZD0530 (saracatinib), BAC, BAN2401 , Benfotiamine, BI409306, Bryostatin 1 , Candesartan, CB-AC-02, Cilostazol, CPC-201 , CT1812, DAOIB, Dronabinol, E2609, Formoterol, hUCB-MSCs, JNJ-54861991 , Levetiracetam, Liraglutide, LY3202626, NewGam 10% IVIG, Nilotinib, ORM-12741 , Pimavanserin, Piromelatine, Posiphen, PQ912, Probucol, Rasagiline, Riluzole, RVT-101 , S47445, Sargramostim, Simvastatin+L-Arginine +Tetrahydrobiopterin (SLAT), STA-1 , SUVN-502, T-817 MA, Temisartan, UB-31 1, Valacyclovir, VX-745, Xanamema. See Cummings et al., Alzheimer's disease drug development pipeline: 2017, Alzheimer's & Dementia, 3:367-384, 2017. In some embodiments, the anti-tau therapy comprises a small molecule or peptide vaccine therapy, or an anti-tau antibody therapy. See U.S. Pat. No. 9,518,101 , which is incorporated by reference in its entirety.

The additional therapeutic agents provided herein can include acetylcholinesterase inhibitors {e.g., donepezil, rivastigmine, galantamine, tacrine, nutritive supplements), N-Methyl-D-aspartate (NMDA) receptor antagonists (e.g., memantine), inhibitors of DNA repair (e.g., pirenzepine or a metabolite thereof), transition metal chelators, growth factors, hormones, non-steroidal anti-inflammatory drugs (NSAID), antioxidants, lipid lowering agents, selective phosphodiesterase inhibitors, inhibitors of tau aggregation, inhibitors of protein kinases, inhibitors of anti-mitochondrial dysfunction drugs, neurotrophins, inhibitors of heat shock proteins, inhibitors of Lipoprotein-associated phospholipase A2, memantine, an anti-apoptotic compound, a metal chelator, an inhibitor of DNA repair, 3-amino-1-propanesulfonic acid (3APS), 1,3-propanedisulfonate (1.3PDS), a secretase activator, a beta-secretase inhibitor, a gamma-secretase inhibitor, a beta-amyloid peptide, a beta-amyloid antibody, a tau peptide, a neurotransmitter, a beta-sheet breaker, an anti-inflammatory molecule; and any pharmaceutically acceptable salts thereof.

The additional therapeutic agents provided herein can include other kinds of anti-inflammatory agents, including but not limited to inhibitors of pro-inflammatory transcription factors e.g., inhibitors of NF-κB [e.g., nafamostat, M013 protein, penetranin, (-)-DHMEQ, IT-603, IT-901 and PBS-1086] and inhibitors of STAT [signal transducer and activator of transcription] proteins [e.g., JAK1, JAK2 and JAK3 inhibitors]), antagonists of the prostaglandin D2 receptor (DPi) or/and the chemoattractant receptor homologous molecule expressed on TH2 cells (CRTH2) (e.g., TS-022), phosphodiesterase (PDE) inhibitors (e.g., PDE4 inhibitors such as apremilast, cilomilast, ibudilast, piclamilast, roflumilast, crisaborole, diazepam, luteolin, mesembrenone, rolipram, AN2728 and E6005), IgE inhibitors (e.g., anti-IgE antibodies such as omalizumab), myeloperoxidase inhibitors (e.g., dapsone), specialized pro-resolving mediators (SPMs) (e.g., metabolites of polyunsaturated fatty acids such as lipoxins, resolvins [including resolvins derived from 5Z,8Z,11Z,14Z,17Z-eicosapentaenoic acid {EPA}, resolvins derived from 4Z,7Z,10Z,13Z,16Z,19Z-docosahexaenoic acid {DHA}, and resolvins derived from 7Z,10Z, 13Z,16Z,19Z-docosahexaenoic acid {n-3 DPA}], protectins/neuroprotectins [including DHA-derived protectins/neuroprotectins and n-3 DPA-derived protectins/neuroprotectins], maresins [including DHA-derived maresins and n-3 DPA-derived maresins], n-3 DPA metabolites, n-6 DPA {4Z,7Z,10Z,13Z,16Z-docosapentaenoic acid} metabolites, oxo-DHA metabolites, oxo-DPA metabolites, docosahexaenoyl ethanolamide metabolites, cyclopentenone prostaglandins [e.g., 412-PGJ2 and 15-deoxy-412, 14-PGJ2], and cyclopentenone isoprostanes [e.g., 5,6-epoxyisoprostane A2 and 5,6-epoxyisoprostane E2]), disease-modifying antirheumatic drugs (DMARDs, e.g., sulfasalazine and mesalazine [5-aminosalicylic acid]), anti-allergic agents (e.g., antihistamines, inhibitors of leukotrienes or receptors therefor or the production thereof, mast cell stabilizers, glucocorticoids, epinephrine [adrenaline] and tranilast), ultraviolet radiation (e.g., ultraviolet A and B), and analogs, derivatives, fragments and salts thereof. The additional therapeutic agents provided herein can include a tau-binding antibody or tau-binding fragment thereof.

Examples of non-steroidal anti-inflammatory drugs (NSAIDs) that can be administered with the NK1R antagonists (e.g., aprepitant) provided herein include, but are not limited to: acetic acid derivatives, such as aceclofenac, bromfenac, diclofenac, etodolac, indomethacin, ketorolac, nabumetone, sulindac, sulindac sulfide, sulindac sulfone and tolmetin; anthranilic acid derivatives (fenamates), such as flufenamic acid, meclofenamic acid, mefenamic acid and tolfenamic acid; enolic acid derivatives (oxicams), such as droxicam, isoxicam, lornoxicam, meloxicam, piroxicam and tenoxicam; propionic acid derivatives, such as fenoprofen, flurbiprofen, ibuprofen, dexibuprofen, ketoprofen, dexketoprofen, loxoprofen, naproxen and oxaprozin; salicylates, such as diflunisal, salicylic acid, acetylsalicylic acid (aspirin), choline magnesium trisalicylate, and salsalate; COX-2-selective inhibitors, such as apricoxib, celecoxib, etoricoxib, firocoxib, fluorocoxibs (e.g., fluorocoxibs A-C), lumiracoxib, mavacoxib, parecoxib, rofecoxib, tilmacoxib (JTE-522), valdecoxib, 4-O-methylhonokiol, niflumic acid, DuP-697, CG100649, GW406381, NS-398, SC-58125, benzothieno[3,2-d]pyrimidin-4-one sulfonamide thio-derivatives, and COX-2 inhibitors derived from *Tribulus terrestris*; other kinds of NSAIDs, such as monoterpenoids (e.g., eucalyptol and phenols [e.g., carvacrol]), anilinopyridinecarboxylic acids (e.g., clonixin), sulfonanilides (e.g., nimesulide), and dual inhibitors of lipooxygenase (e.g., 5-LOX) and cyclooxygenase (e.g., COX-2) [e.g., chebulagic acid, licofelone, 2-(3,4,5-trimethoxyphenyl)-4-(N-methylindo1- 3-yl)thiophene, and di-tert-butylphenol-based compounds (e.g., DTPBHZ, DTPINH, DTPNHZ and DTPSAL)]; and analogs, derivatives and salts thereof.

As disclosed herein, co-administration of particular ratios and/or amounts of an NK1R antagonist (e.g., aprepitant) and one or more additional therapeutic agents (e.g., anti-AD agents) can result in synergistic effects in treating or preventing AD (e.g., reducing or preventing AD symptoms). These synergistic effects can be such that the one or more effects of the combination compositions are greater than the one or more effects of each component alone at a comparable dosing level, or they can be greater than the predicted sum of the effects of all of the components at a comparable dosing level, assuming that each component acts independently. The synergistic effect can be, be about, be greater than, or be greater than about, 5%, 10%, 20%, 30%, 50%, 75%, 100%, 110%, 120%, 150%, 200%, 250%, 350%, or 500% better than the effect of treating a subject with one of the components alone, or the additive effects of each of the components when administered individually. The effect can be any of the measurable effects described herein. The composition comprising a plurality of therapeutic agents can be such that the synergistic effect is a reduction in AD symptoms is reduced to a greater degree as compared to the sum of the effects of administering each component, determined as if each component exerted its effect independently, also referred to as the predicted additive effect herein. For example, if a composition comprising therapeutic agent (a) yields an effect of a 20% reduction in AD symptoms and a composition comprising therapeutic agent (b) yields an effect of 50% reduction in AD symptoms, then a composition comprising both therapeutic agent (a) and therapeutic agent (b) would have a synergistic effect if the combination composition's effect on AD symptoms was greater than 70%.

A synergistic combination composition can have an effect that is greater than the predicted additive effect of administering each therapeutic agent of the combination composition alone as if each therapeutic agent exerted its effect independently. For example, if the predicted additive effect is 70%, an actual effect of 140% is 70% greater than the predicted additive effect or is 1 fold greater than the predicted additive effect. The synergistic effect can be at least, or at least about, 20%, 50%, 75%, 90%, 100%, 150%, 200% or 300% greater than the predicted additive effect. In some embodiments, the synergistic effect can be at least, or at least about, 0.2, 0.5, 0.9, 1.1, 1.5, 1.7, 2, or 3 fold greater than the predicted additive effect.

In some embodiments, the synergistic effect of the combination compositions can also allow for reduced dosing amounts, leading to reduced side effects to the subject and reduced cost of treatment. Furthermore, the synergistic effect can allow for results that are not achievable through any other treatments. Therefore, proper identification, specification, and use of combination compositions can allow for significant improvements in the reduction and prevention of AD symptoms.

Methods to Identify Subjects for Risk of or having Alzheimer's Disease

A subject in need of identifying the presence of AD phenotype is any subject at risk of, or suspected of, having AD. A subject at risk of having AD can be, for example, a subject having one or more risk factors for AD. Risk factors for AD include, but are not limited to, age, family history, heredity and brain injury. Other risk factors will be apparent to the skilled artisan. A subject suspected of having AD can be, for example, a subject having one or more clinical symptoms of AD. A variety of clinical symptoms of AD are known in the art. Examples of such symptoms include, but are not limited to, memory loss, depression, anxiety, language disorders (e.g., anomia) and impairment in their visuospatial skills. Some embodiments of the methods provided herein comprise one or more patient identification steps (e.g., identifying subjects amenable to treatment using the methods as disclosed herein). Some embodiments of the methods provided herein comprise identifying subsets of subjects suitable for treatment using the methods as disclosed herein.

Subjects amenable to treatment using the methods as disclosed herein include subjects at risk of a neurodegenerative disease, for example Alzheimer's disease but not showing symptoms, as well as subjects showing symptoms of the neurodegenerative disease, for example subjects with symptoms of Alzheimer's disease. Subjects can be screened for their likelihood of having or developing Alzheimer's disease based on a number of biochemical and genetic markers.

In some embodiments, one can diagnose a subject with increased risk of developing Alzheimer's disease using genetic markers for Alzheimer's disease. Genetic abnormality in a few families has been traced to chromosome 21 (St. George-Hyslop et al., Science 235:885-890, 1987). One genetic marker is, for example mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of Alzheimer's disease, hypercholesterolemia or atherosclerosis. Subjects with APP, PS1 or PS2 mutations are highly likely to develop Alzheimer's disease. ApoE is a susceptibility gene, and subjects with the e4 isoform of ApoE (ApoE4 isoform) have an increased risk of developing Alzheimer's disease. Test for subjects with ApoE4 isoform are disclosed in U.S. Pat. No. 6,027,896, which is incorporated in its entirety herein by reference. Other genetic links have been associated with increased risk of Alzheimer's disease, for example variances in the neuronal sortilin-related receptor SORL1 may have increased likelihood of developing late-onset Alzheimer's disease (Rogaeva at al., Nat Genet. 2007 February; 39(2):168-77). Other potential Alzheimer disease susceptibility genes, include, for example ACE, CHRNB2, CST3, ESR1, GAPDHS, IDE, MTHFR, NCSTN, PRNP, PSEN1, TF, TFAM and TNF and be used to identify subjects with increased risk of developing AD (Bertram et al, Nat Genet. 2007 January; 39(1): 17-23), as well as variances in the alpha-T catenin (VR22) gene (Bertram et al, J Med Genet. 2007 January; 44(1):e63) and Insulin-degrading enzyme (IDE) and Kim et al, J Biol Chem. 2007; 282:7825-32).

In some embodiments, one can diagnose a subject with increased risk of developing Alzheimer's disease on the basis of a simple eye test, where the presence of cataracts and/or amyloid beta in the lens identifies a subject with increased risk of developing Alzheimer's disease. Methods to detect Alzheimer's disease include using a quasi-elastic light scattering device (Goldstein et al., Lancet. 2003; 12; 361:1258-65) from Neuroptix, using Quasi-Elastic Light Scattering (QLS) and Fluorescent Ligand Scanning (FLS) and a Neuroptix™ QEL scanning device, to enable non-invasive quantitative measurements of amyloid aggregates in the eye, to examine and measure deposits in specific areas of the lens as an early diagnostic for Alzheimer's disease. Methods to diagnose a subject at risk of developing Alzheimer's disease using such a method of non-invasive eye test are disclosed in U.S. Pat. No. 7,107,092, which is incorporated in its entirety herein by reference.

Individuals presently suffering from Alzheimer's disease can be recognized, for example, from characteristic dementia, as well as the presence of risk factors described above. In addition, a number of diagnostic tests are available for identifying individuals who have AD. These include measurement of CSF tau and Ax3b242 levels. Elevated tau and decreased Ax3b242 levels signify the presence of Alzheimer's Disease.

There are at least two alternative "criteria" which are utilized to clinically diagnose Alzheimer's disease: the DSM-IIIR criteria and the NINCDS-ADRDA criteria (which is an acronym for National Institute of Neurological and Communicative Disorders and Stroke (NINCDS) and the Alzheimer's Disease and Related Disorders Association (ADRDA); see McKhann et al., Neurology 34:939-944, 1984). Briefly, the criteria for diagnosis of Alzheimer's Disease under DSM-IIIR include (1) dementia, (2) insidious onset with a generally progressive deteriorating course, and (3) exclusion of all other specific causes of dementia by history, physical examination, and laboratory tests. Within the context of the DSM-IIIR criteria, dementia is understood to involve "a multifaceted loss of intellectual abilities, such as memory, judgment, abstract thought, and other higher cortical functions, and changes in personality and behaviour." (DSM-IIR, 1987).

The NINCDS-ADRDA criteria set forth three categories of Alzheimer's Disease, including "probable," "possible," and "definite" AD. Clinical diagnosis of "possible" Alzheimer's disease may be made on the basis of a dementia syndrome, in the absence of other neurologic, psychiatric or systemic disorders sufficient to cause dementia. Criteria for the clinical diagnosis of "probable" AD include (a) dementia established by clinical examination and documented by a test such as the Mini-Mental test (Foldstein et al., J. Psych. Res. 12:189-198, 1975); (b) deficits in two or more areas of cognition; (c) progressive worsening of memory and other cognitive functions; (d) no disturbance of consciousness; (e) onset between ages 40 and 90, most often after age 65; and (f) absence of systemic orders or other brain diseases that could account for the dementia. The criteria for definite diagnosis of AD include histopathologic evidence obtained from a biopsy, or after autopsy. Since confirmation of definite AD requires histological examination from a brain biopsy specimen (which is often difficult to obtain), it is rarely used for early diagnosis of Alzheimer's disease.

In some embodiments, one can use neuropathologic diagnosis of AD, where the numbers of plaques and tangles in the neurocortex (frontal, temporal, and parietal lobes), hippocampus and amygdala are analyzed (Khachaturian, Arch. Neurol. 42:1097-1105; Esiri, "Anatomical Criteria for the Biopsy diagnosis of Alzheimer's Disease," Alzheimer's Disease, Current Research in Early Diagnosis, Becker and Giacobini (eds.), pp. 239-252, 1990).

In some embodiments, one can use quantitative electroencephalographic analysis (EEG) to diagnose AD. This method employs Fourier analysis of the beta, alpha, theta, and delta bands (Riekkinen et al., "EEG in the Diagnosis of Early Alzheimer's Disease," Alzheimer's Disease, Current Research in Early Diagnosis, Becker and Giacobini (eds.), pp. 159-167, 1990) for diagnosis of Alzheimer's Disease.

In some embodiments, one can diagnose AD by quantifying the degree of neural atrophy, since such atrophy is generally accepted as a consequence of AD. Examples of these methods include computed tomographic scanning (CT), and magnetic resonance imaging (MM) (Leedom and Miller, "CT, MRI, and NMR Spectroscopy in Alzheimer's Disease," Alzheimer's Disease, Current Research in Early Diagnosis, Becker and Giacobini (eds.), pp. 297-313, 1990).

In some embodiments, one can diagnose AD by assessing decreased cerebral blood flow or metabolism in the posterior temporoparietal cerebral cortex by measuring decreased blood flow or metabolism by positron emission tomography (PET) (Parks and Becker, "Positron Emission Tomography and Neuropsychological Studies in Dementia," Alzheimer's Disease's, Current Research in Early Diagnosis, Becker and Giacobini (eds.), pp. 315-327, 1990), single photon emission computed tomography (SPECT) (Mena et al., "SPECT Studies in Alzheimer's Type Dementia Patients," Alzheimer's Disease, Current Research in Early Diagnosis, Becker and Giacobini (eds.), pp. 339-355, 1990), and xenon inhalation methods (Jagust et al., Neurology 38:909-912; Prohovnik et al., Neurology 38:931-937; and Waldemar et al., Senile Dementias: II International Symposium, pp. 399407, 1988).

In some embodiments, one can immunologically diagnose AD (Wolozin, "Immunochemical Approaches to the Diagnosis of Alzheimer's Disease," Alzheimer's Disease, Current Research in Early Diagnosis, Becker and Giacobini (eds.), pp. 217-235, 1990). Wolozin and coworkers (Wolozin et al., Science 232:648-650, 1986) produced a monoclonal antibody "Alz50," that reacts with a 68-kDa protein "A68," which is expressed in the plaques and neuron tangles of patients with AD. Using the antibody Alz50 and Western blot analysis, A68 was detected in the cerebral spinal fluid (CSF) of some AD patients and not in the CSF of normal elderly patients (Wolozin and Davies, Ann. Neurol. 22:521-526, 1987).

In some embodiments, one can diagnose AD using neurochemical markers of AD. Neurochemical markers which have been associated with Alzheimer's Disease include reduced levels of acetylcholinesterase (Giacobini and Sugaya, "Markers of Cholinergic Dysfunction in Alzheimer's Disease," Alzheimer's Disease, Current Research in Early Diagnosis, Becker and Giacobini (eds.), pp. 137-156, 1990), reduced somatostatin (Tamminga et al., Neurology 37:161-165, 1987), a negative relation between serotonin and 5-hydroxyindoleacetic acid (Volicer et al., Arch Neurol. 42:127-129, 1985), greater probenecid-induced rise in homovanyllic acid (Gibson et al., Arch. Neurol. 42:489-492, 1985) and reduced neuron-specific enolase (Cutler et al., Arch. Neurol. 43:153-154, 1986).

Compositions and Methods of Administration

There are provided, in some embodiments, kits comprising: a NK1R antagonist (e.g., aprepitant) or a pharmaceutically acceptable salt, solvate, stereoisomer, or prodrug thereof, and a label indicating that the kit is for preventing, delaying the onset of, or treating Alzheimer's disease (AD).

There are provided, in some embodiments, compositions comprising: a NK1R antagonist (e.g., aprepitant) or a pharmaceutically acceptable salt, solvate, stereoisomer, or prodrug thereof for use in treating AD. The composition can comprise: a NK1R antagonist (e.g., aprepitant) or a pharmaceutically acceptable salt, solvate, stereoisomer, or prodrug thereof for use in delaying or reducing the likelihood of onset of AD. The composition can comprise: a NK1R antagonist (e.g., aprepitant) or a pharmaceutically acceptable salt, solvate, stereoisomer, or prodrug thereof for use in treating, preventing, or reversing cognitive decline in clinical or pre-clinical AD. The composition can comprise: a NK1R antagonist (e.g., aprepitant) or a pharmaceutically acceptable salt, solvate, stereoisomer, or prodrug thereof for use in delaying or reversing the progression of AD.

The composition can be a pharmaceutical composition comprising a NK1R antagonist (e.g., aprepitant) or a pharmaceutically acceptable salt, solvate, stereoisomer, or prodrug thereof, and one or more pharmaceutically acceptable excipients. In some embodiments, the composition is administered to the subject by intravenous administration, nasal administration, pulmonary administration, oral administration, parenteral administration, or nebulization. In some embodiments, the composition is in the form of powder, pill, tablet, microtablet, pellet, micropellet, capsule, capsule containing microtablets, film, disintegrating tablet, liquid, aerosols, or nanoparticles. In some embodiments, the composition is administered to the subject once, twice, or three times a day. In some embodiments, the composition is administered to the subject once every day, every two days, or every three days. In some embodiments, the composition is administered to the subject over the course of at least two weeks, at least three weeks, at least four weeks, at least five weeks, or for indefinite duration. In some embodiments, the composition is administered to the subject at an effective daily dose of aprepitant or a pharmaceutically acceptable salt, solvate, stereoisomer, or prodrug thereof at from 10 mg to 250 mg.

The therapeutically effective amount and the frequency of administration of, and the length of treatment with, the NK1R antagonist (e.g., aprepitant) may depend on various factors, including the nature and the severity of the AD, the potency of the NK1R antagonist, the mode of administration, the age, the body weight, the general health, the gender and the diet of the subject, and the response of the subject to the treatment, and can be determined by a medical professional. In some embodiments, a therapeutically effective amount of the NK1R antagonist (e.g., aprepitant) for treating or preventing AD as described herein is about 0.1-250 mg, 0.1-200 mg, 0.1-150 mg, 0.1-100 mg, 0.1-50 mg, 0.1-30 mg, 0.5-20 mg, 0.5-10 mg or 1-10 mg (e.g., per day or per dose), or any amount therebetween, or as deemed appropriate by a medical professional, which can be administered in a single dose or in divided doses. In some embodiments, the therapeutically effective dose (e.g., per day or per dose) of the NK1R antagonist (e.g., aprepitant) for treating or preventing AD as described herein is about 0.1 to about 1 mg (e.g., about 0.1 mg, 0.5 mg or 1 mg), about 1-5 mg (e.g., about 1 mg, 2 mg, 3 mg, 4 mg or 5 mg), about 5-10 mg (e.g., about 5 mg, 6 mg, 7 mg, 8 mg, 9 mg or 10 mg), about 10-20 mg (e.g., about 10 mg, 15 mg or 20 mg), about 20-30 mg (e.g., about 20 mg, 25 mg or 30 mg), about 30-40 mg (e.g., about 30 mg, 35 mg or 40 mg), about 40-50 mg (e.g., about 40 mg, 45 mg or 50 mg), about 50-100 mg (e.g., about 50 mg, 60 mg, 70 mg, 80 mg, 90 mg or 100 mg), about 100-150 mg (e.g., about 100 mg, 125 mg or 150 mg), about 150-200 mg (e.g., about 150 mg, 175 mg or 200 mg), or about 200-250 mg (e.g., about 200 mg, 225 mg, or 250 mg), or any amount therebetween. In some embodiments, the therapeutically effective dose of the NK1R antagonist (e.g., aprepitant) is administered one or more (e.g., two, three or more) times a day, or once every two days, or once every three days, or once a week, or twice a week, or thrice a week, or as deemed appropriate by a medical professional. In some embodiments, the composition comprises a therapeutically or prophylactically effective amount of aprepitant or a pharmaceutically acceptable salt, solvate, stereoisomer, or prodrug thereof.

The NK1R antagonist (e.g., aprepitant) can also be dosed in an irregular manner. For example, the NK1R antagonist can be administered once, twice or thrice in a period of two weeks, three weeks or a month in an irregular manner. Furthermore, the NK1R antagonist (e.g., aprepitant) can be taken pro re rata (as needed). For instance, the NK1R antagonist can be administered 1, 2, 3, 4, 5 or more times, whether in a regular or irregular manner, until at least one symptom of Alzheimer's disease improves. Once relief from AD is achieved, dosing of the NK1R antagonist can optionally be discontinued or reduced in amount or frequency. If AD returns, administration of the NK1R antagonist, whether in a regular or irregular manner, can be resumed. The appropriate dosage of, frequency of dosing of and length of treatment with the NK1R antagonist can be determined by a medical professional.

In some embodiments, the NK1R antagonist (e.g., aprepitant) is administered under a chronic dosing regimen. In some embodiments, a therapeutically effective amount of the NK1R antagonist (e.g., aprepitant) is administered over a period of at least about 6 weeks, 2 months, 10 weeks, 3 months, 4 months, 5 months, 6 months, 1 year, 1.5 years, 2 years, 3 years or longer (e.g., at least about 6 weeks, 2 months, 3 months or 6 months).

The NK1R antagonist (e.g., aprepitant) can also be used prophylactically to treat or prevent AD. The prophylactically effective amount of an NK1R antagonist (e.g., aprepitant) can be any therapeutically effective amount of the NK1R antagonist described herein.

The NK1R antagonist (e.g., aprepitant) can be administered via any suitable route. Potential routes of administration of the NK1R antagonist include without limitation oral, parenteral (including intramuscular, subcutaneous, intradermal, intravascular, intravenous, intraarterial, intramedullary and intrathecal), intracavitary, intraperitoneal, and topical (including dermal/epicutaneous, transdermal, mucosal, transmucosal, intranasal [e.g., by nasal spray or drop], intraocular [e.g., by eye drop], pulmonary [e.g., by oral or nasal inhalation], buccal, sublingual, rectal and vaginal). In some embodiments, the NK1R antagonist (e.g., aprepitant) is administered orally (e.g., as a capsule or tablet, optionally with an enteric coating). In other embodiments, the NK1R antagonist (e.g., aprepitant) is administered parenterally (e.g., intravenously, subcutaneously or intradermally). In further embodiments, the NK1R antagonist (e.g., aprepitant) is administered topically (e.g., dermally/epicutaneously, transdermally, mucosally, transmucosally, buccally or sublingually).

The NK1R antagonist (e.g., aprepitant) can be administered without food. In some embodiments, the NK1R antagonist (e.g., aprepitant) is administered at least about 1 or 2 hours before or after a meal. In some embodiments, the NK1R antagonist (e.g., aprepitant) is administered at least about 2 hours after an evening meal. The NK1R antagonist can also be taken substantially concurrently with food (e.g., less than about 30 minutes or 1 hour before or after a meal, or with a meal). The aprepitant can be in a form of oral soluble film (OSF), and optionally in a strength of 5 mg, 30 mg, or 60 mg. The aprepitant OSF can be stored under a USP Controlled Room Temperature, for example at 20-25° C. (68-77° F.); excursions permitted to 15-30° C. (59-86° F.).

In some embodiments, for example where a more rapid establishment of a therapeutic level of the NK1R antagonist (e.g., aprepitant) is desired, the NK1R antagonist is administered under a dosing schedule in which a loading dose is administered, followed by (i) one or more additional loading doses and then one or more therapeutically effective maintenance doses, or (ii) one or more therapeutically effective maintenance doses without an additional loading dose, as deemed appropriate by a medical professional. A loading dose of a drug is typically larger (e.g., about 1.5, 2, 3, 4 or 5 times larger) than a subsequent maintenance dose and is designed to establish a therapeutic level of the drug more quickly. The one or more therapeutically effective maintenance doses can be any therapeutically effective dose described herein. In some embodiments, the loading dose is about 1.5 times, about two times, about three times, about four times, or about five times greater than the maintenance dose. In some embodiments, the loading dose is about three times greater than the maintenance dose. In some embodiments, a loading dose of the NK1R antagonist (e.g., aprepitant) is administered, followed by administration of a maintenance dose of the NK1R antagonist (e.g., aprepitant) after an appropriate time (e.g., after about 12 or 24 hours) and thereafter for the duration of therapy—e.g., a loading dose of the NK1R antagonist is administered on day 1 and a maintenance dose is administered on day 2 and thereafter for the duration of therapy. In some embodiments, the NK1R antagonist (e.g., aprepitant) is administered in a loading, dose of about 1.5-30 mg, or about 1.5 mg, or about 3, or about 15, or about 30 mg (e.g., 3× about 0.5-10 mg, or about 0.5, or about 1, or about 5, or about 10 mg) orally (e.g., as a film, tablet or capsule) on day 1, followed by a maintenance dose of about 0.5-10 mg, or about 0.5 mg, or about 1 mg, or about 5 mg, or about 10 mg orally (e.g., as a film, tablet or capsule) once daily, optionally at bedtime, for at least about 2 weeks, 3 weeks, 1 month (4 weeks), 5 weeks, 6 weeks, 7 weeks, 2 months (8 weeks), 9, weeks, 10 weeks, 11 weeks, 3 months, 4 months, 5 months, 6 months, 7 months, 8 months, 9 months, 10 months, 11 months, 1 year, 1.5 years, 2 years, 2.5 years, 3 years or longer (e.g., at least about 6 weeks, 2 months, 3 months or 6 months). In some embodiments, the NK1R antagonist (e.g., aprepitant) is administered in a loading dose of about 15 mg (e.g., 3×about 5 mg) orally (e.g., as a tablet) on day 1, followed by a maintenance dose of about 5 mg orally (e.g., as a tablet) once daily, optionally at bedtime, for at least about 2 weeks, 1 month, 6 weeks, 2 months, 3 months, 6 months, 1 year, 1.5 years, 2 years, 3 years or longer (e.g., at least about 6 weeks, 2 months, 3 months or 6 months).

In some embodiments, a first loading dose of the NK1R antagonist (e.g., aprepitant) is administered on day 1, a second loading dose is administered on day 2, and a maintenance dose is administered on day 3 and thereafter for the duration of therapy. In some embodiments, the first loading dose is about three times greater than the maintenance dose, and the second loading dose is about two times greater than the maintenance dose.

As disclosed herein, the therapeutic agent (e.g., NK1R antagonist) can be formulated for administration in a pharmaceutical composition comprising a physiologically acceptable surface active agent, carrier, diluent, excipient, smoothing agent, suspension agent, film forming substance, coating assistant, or a combination thereof. In some embodiments, the therapeutic agent (e.g., NK1R antagonist) are formulated for administration with a pharmaceutically acceptable carrier or diluent. The therapeutic agent (e.g., NK1R antagonist) can be formulated as a medicament with a standard pharmaceutically acceptable carrier(s) and/or excipient(s) as is routine in the pharmaceutical art. The exact nature of the formulation will depend upon several factors including the desired route of administration. In some embodiments, the NK1R antagonist is formulated for oral, intravenous, intragastric, intravascular or intraperitoneal administration.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically- acceptable carriers or components thereof, are sugars, such as lactose, glucose and sucrose: starches, such as corn starch and potato starch; cellulose and its derivatives, such as sodium carboxymethyl cellulose, powdered tragacanth; malt; gelatin; talc; solid lubricants, such as stearic acid and magnesium stearate; calcium sulfate; vegetable oils, such as peanut oil, cottonseed oil, sesame oil, olive oil, com oil and oil of theobroraa; polyols such as propylene glycol, glycerine, sorbitol, mannitol, and polyethylene glycol; aiginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject therapeutic agent is generally determined by the way the composition is to be administered.

The compositions described herein are preferably provided in unit dosage form. The preparation of a single or unit dosage form, however, does not imply that the dosage form is administered once per day or once per course of therapy. In some embodiments, unit dosage forms may be administered once, twice, thrice or more per day and may be administered as an infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the therapeutic agent (e.g., NK1R antagonist). The amount of carrier employed in conjunction with the therapeutic agent (e.g., NK1R antagonist) is sufficient to provide a practical quantity of material for administration per unit dose of the therapeutic agent (e.g., NK1R antagonist). Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et Ai, Pharmaceutical Dosage Forms: Tablets (1989), and Ansel, Introduction to Pharmaceutical Dosage Forms 8th Edition (2004).

Various oral dosage forms can be used, including such solid forms as tablets, capsules, films, and granules. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include, for example, ethanol, glycerol, propylene glycol, polyethylene glycol, liquid sucrose, sorbitol and water. For a suspension, typical suspending agents include, for example, sodium carboxymethyl cellulose, AVICEL RC-591, tragacanth and sodium alginate; typical wetting agents include, for example, lecithin and polvsorbate 80; and typical preservatives include, for example, methyl paraben and sodium benzoate. Peroral liquid compositions may also contain one or more components such as sweeteners, flavoring agents and colorants disclosed above.

Other compositions useful for attaining systemic delivery of the subject therapeutic agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

For topical use, creams, ointments, gels, solutions or suspensions, etc., containing the therapeutic agent (e.g., NK1R antagonist) disclosed herein are employed. Topical formulations may generally be comprised of a pharmaceutical carrier, co-solvent, emulsifier, penetration enhancer, preservative system, and emollient.

For intravenous administration, the therapeutic agent (e.g., NK1R antagonist) and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include, for example, sodium bisulfite, acetone sodium bisulfite, sodium formaldehyde, suifoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, PDA J Pharm Sci and Tech 1998, 52 238-31 1 and Nema et al., Excipients and Their Role in Approved Injectable Products: Current Usage and Future Directions, PDA J Pharm Sci and Tech 2011, 65 287-332, both of which are incorporated herein by reference in their entirety. Antimicrobial agents may also be included to achieve a bacteriostatic or fungistatic solution, including but not limited to phenyl mercuric nitrate, thimerosal, benzethonium chloride, benzalkonium chloride, phenol, cresol, and chlorobutanol.

The compositions for intravenous administration may be provided in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a therapeutic agent (e.g., NK1R antagonist) described herein and another agent, the combination may be provided as a mixture, or the two agents may be mixed prior to administration, or the two agents may be administered separately.

In some embodiments, in non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 0.1 mg/kg and 4000 mg/kg body weight, preferably between about 2 mg/kg and 200 mg/kg body weight. Alternatively dosages may be based and calculated upon the surface area of the patient, as understood by those of skill in the art.

Depending on the severity and responsiveness of the condition to be treated, dosing can also be a single administration of a slow release composition, with the course of treatment lasting from several days to several weeks or until a cure is effected or diminution of the disease state is achieved. The amount of a composition to be administered will, of course, be dependent on many factors including the subject being treated, the severity of the affliction, the manner of administration, the judgment of the prescribing physician. The therapeutic agent (e.g., NK1R antagonist) or combination of therapeutic agents disclosed herein may be administered orally or via injection at a dose from 0.1 mg/kg to 4000 mg/kg of the patient's body weight per day. The dose range for adult humans can be from 1 g to 200 g/day. Tablets or other forms of presentation provided in discrete units may conveniently contain an amount of the therapeutic agent (e.g., NK1R antagonist) or combination of therapeutic agents disclosed herein which is effective at such dosage or as a multiple of the same, for instance, units containing 1 g to 60 g (for example, from about 5 g to 20 g, from about 10 g to 50 g, from about 20 g to 40 g, or from about 25 g to 35 g). The precise amount of therapeutic agent administered to a patient will be the responsibility of a medical professional. However, the dose employed will depend on a number of factors, including the age and sex of the patient, the precise disorder being treated, and its severity. Additionally, the route of administration may vary depending on the condition and its severity. A typical dose of the therapeutic agent (e.g., NK1R antagonist) can be from 0.02 g to 1.25 g per kg of body weight, for example from 0.1 g to 0.5 g per kg of body weight, depending on such parameters. In some embodiments, a dosage of the therapeutic agent (e.g., NK1R antagonist) can be from 1 g to 100 g, for example, from 10 g to 80 g, from 15 g to 60 g, from 20 g to 40 g, or from 25 g to 35 g. In A physician will be able to determine the required dosage of the therapeutic agent (e.g., NK1R antagonist) for a particular subject.

The exact formulation, route of administration and dosage for the pharmaceutical compositions of the therapeutic agent (e.g., NK1R antagonist) or combination of therapeutic agents disclosed herein can be chosen by the individual physician in view of the patient's condition. Typically, the dose range of the composition administered to the patient can be from about 0.1 to about 4000 mg/kg of the patient's body weight. The dosage may be a single one or a series of two or more given in the course of one or more days, as is needed by the patient. In instances where human dosages for therapeutic agents have been established for at least some condition, the present disclosure will use those same dosages, or dosages that are between about 0.1% and about 5000%, more preferably between about 25% and about 1000% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that a medical professional would know how to and when to terminate, interrupt, or adjust administration due to toxicity or organ dysfunctions. Conversely, a medical professional would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. In cases of administration of a pharmaceutically acceptable salt, dosages may be calculated as the free base. In some embodiments, the composition is administered 1 to 4 times per day. Alternatively the compositions disclosed herein may be administered by continuous intravenous infusion, e.g., at a dose of each active ingredient up to 100 g per day. As will be understood by those of skill in the art, in certain situations it may be necessary to administer the compositions disclosed herein in amounts that exceed, or even far exceed, the above-stated, preferred dosage range in order to effectively and aggressively treat particularly aggressive diseases or infections. In some embodiments, the therapeutic agent (e.g., NK1R antagonist) or combination of therapeutic agents disclosed herein will be administered for a period of continuous therapy, for example for a week or more, or for months or years.

In some embodiments, the dosing regimen of the therapeutic agent (e.g., NK1R antagonist) or combination of therapeutic agents disclosed herein is administered for a period of time, which time period can be, for example, from at least about 1 week to at least about 4 weeks, from at least about 4 weeks to at least about 8 weeks, from at least about 4 weeks to at least about 12 weeks, from at least about 4 weeks to at least about 16 weeks, or longer. The dosing regimen of the therapeutic agent (e.g., NK1R antagonist) or combination of therapeutic agents disclosed herein can be administered three times a day, twice a day, daily, every other day, three times a week, every other week, three times per month, once monthly, substantially continuously or continuously.

The NK1R antagonist (e.g., aprepitant) can be administered alone or in the form of a composition (e.g., a pharmaceutical composition). In some embodiments, a pharmaceutical composition comprises an NK1R antagonist (e.g., aprepitant) or a pharmaceutically acceptable salt, solvate, hydrate, clathrate, polymorph, prodrug or metabolite thereof, and one or more pharmaceutically acceptable carriers or excipients. The composition can optionally contain one or more additional therapeutic agents as described herein. A pharmaceutical composition contains a therapeutically effective amount of a therapeutic agent (e.g., an NK1R antagonist, such as aprepitant) and one or more pharmaceutically acceptable carriers or excipients, and is formulated for administration to a subject for therapeutic use. For purposes of the content of a pharmaceutical composition, the terms "therapeutic agent", "active ingredient", "active agent" and "drug" encompass prodrugs.

A pharmaceutical composition contains a therapeutic agent (e.g., an NK1R antagonist, such as aprepitant) in substantially pure form. In some embodiments, the purity of the therapeutic agent is at least about 95%, 96%, 97%, 98% or 99%. In some embodiments, the purity of the therapeutic agent is at least about 98% or 99%. In addition, a pharmaceutical composition is substantially free of contaminants or impurities. In some embodiments, the level of contaminants or impurities other than residual solvent in a pharmaceutical composition is no more than about 5%, 4%, 3%, 2% or 1% relative to the combined weight of the intended active and inactive ingredients. In some embodiments, the level of contaminants or impurities other than residual solvent in a pharmaceutical composition is no more than about 2% or 1% relative to the combined weight of the intended active and inactive ingredients. Pharmaceutical compositions generally are prepared according to current good manufacturing practice (GMP), as recommended or required by, e.g., the Federal Food, Drug, and Cosmetic Act § 501(a)(2)(B) and the International Conference on Harmonisation Q7 Guideline.

Pharmaceutically acceptable carriers and excipients include pharmaceutically acceptable materials, vehicles and substances. Non-limiting examples of excipients include liquid and solid fillers, diluents, binders, lubricants, glidants, solubilizers, surfactants, dispersing agents, disintegration agents, emulsifying agents, wetting agents, suspending agents, thickeners, solvents, isotonic agents, buffers, pH adjusters, stabilizers, preservatives, antioxidants, antimicrobial agents, antibacterial agents, antifungal agents, absorption- delaying agents, sweetening agents, flavoring agents, coloring agents, adjuvants, encapsulating materials and coating materials. The use of such excipients in pharmaceutical formulations is known in the art. For example, conventional vehicles and carriers include without limitation oils (e.g., vegetable oils, such as sesame oil), aqueous solvents (e.g., saline, phosphate-buffered saline [PBS] and isotonic solutions [e.g., Ringer's solution]), and solvents (e.g., dimethyl sulfoxide [DMSO] and alcohols [e.g., ethanol, glycerol and propylene glycol]). Except insofar as any conventional carrier or excipient is incompatible with the active ingredient, the disclosure encompasses the use of conventional carriers and excipients in formulations containing a therapeutic agent (e.g., an NK1R antagonist, such as aprepitant). See, e.g., Remington: The Science and Practice of Pharmacy, 21st Ed., Lippincott Williams & Wilkins (Philadelphia, Pennsylvania [2005]); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press (Boca Raton, Florida., 2004).

Proper formulation can depend on various factors, such as the mode of administration chosen. Potential modes of administration of pharmaceutical compositions comprising an NK1R antagonist (e.g., aprepitant) include without limitation oral, parenteral (including intramuscular, subcutaneous, intradermal, intravascular, intravenous, intraarterial, intraperitoneal, intramedullary, intrathecal and topical), intracavitary, and topical (including dermal/epicutaneous, transdermal, mucosal, transmucosal, intranasal [e.g., by nasal spray or drop], pulmonary [e.g., by oral or nasal inhalation], buccal, sublingual, rectal [e.g., by suppository], and vaginal [e.g., by suppository]).

As an example, formulations of an NK1R antagonist (e.g., aprepitant) suitable for oral administration can be presented as, e.g., boluses; tablets, capsules, pills, sachets or lozenges; as powders or granules; as semisolids, electuaries, pastes or gels; as solutions or suspensions in an aqueous liquid or/and a non-aqueous liquid; or as oil-in-water liquid emulsions or water- in-oil liquid emulsions.

Tablets can contain an NK1R antagonist (e.g., aprepitant) in admixture with, e.g., a filler or inert diluent (e.g., calcium carbonate, calcium phosphate, lactose, mannitol or microcrystalline cellulose), a binding agent (e.g., a starch, gelatin, acacia, alginic acid or a salt thereof, or microcrystalline cellulose), a lubricating agent (e.g., stearic acid, magnesium stearate, talc or silicon dioxide), and a disintegrating agent (e.g., crospovidone, croscarmellose sodium or colloidal silica), and optionally a surfactant (e.g., sodium lauryl sulfate). The tablets can be uncoated or can be coated with, e.g., an enteric coating that protects the active ingredient from the acidic environment of the stomach, or with a material that delays disintegration and absorption of the active ingredient in the gastrointestinal tract and thereby provides a sustained action over a longer time period. In some embodiments, a tablet comprises an NK1R antagonist (e.g., aprepitant), mannitol, microcrystalline cellulose, magnesium stearate, silicon dioxide, croscarmellose sodium and sodium lauryl sulfate, and optionally lactose monohydrate, and the tablet is optionally film-coated (e.g., with Opadry®).

Push-fit capsules or two-piece hard gelatin capsules can contain an NK1R antagonist (e.g., aprepitant) in admixture with, e.g., a filler or inert solid diluent (e.g., calcium carbonate, calcium phosphate, kaolin or lactose), a binder (e.g., a starch), a glidant or lubricant (e.g., talc or magnesium stearate), and a disintegrant (e.g., crospovidone), and optionally a stabilizer or/and a preservative. For soft capsules or single-piece gelatin capsules, an NK1R antagonist (e.g., aprepitant) can be dissolved or suspended in a suitable liquid (e.g., liquid polyethylene glycol or an oil medium, such as a fatty oil, peanut oil, olive oil or liquid paraffin), and the liquid-filled capsules can contain one or more other liquid excipients or/and semi- solid excipients, such as a stabilizer or/and an amphiphilic agent (e.g., a fatty acid ester of glycerol, propylene glycol or sorbitol).

Compositions for oral administration can also be formulated as solutions or suspensions in an aqueous liquid or/and a non-aqueous liquid, or as oil-in-water liquid emulsions or water-in-oil liquid emulsions. Dispersible powder or granules of an NK1R antagonist (e.g., aprepitant) can be mixed with any suitable combination of an aqueous liquid, an organic solvent or/and an oil and any suitable excipients (e.g., any combination of a dispersing agent, a wetting agent, a suspending agent, an emulsifying agent or/and a preservative) to form a solution, suspension or emulsion.

The NK1R antagonist (e.g., aprepitant) can be contained in an amphiphilic vehicle of a liquid or semi-solid formulation for oral administration which provides improved solubility, stability and bioavailability of the NK1R antagonist, as described in US2010/0209496. The amphiphilic vehicle contains a solution, suspension, emulsion (e.g., oil-in-water emulsion) or semi-solid mixture of the NK1R antagonist (e.g., aprepitant) admixed with liquid or/and semi-solid excipients which fills an encapsulated dosage form (e.g., a hard gelatin capsule or a soft gelatin capsule containing a plasticizer [e.g., glycerol or/and sorbitol]). In some embodiments, the amphiphilic vehicle comprises an amphiphilic agent selected from fatty acid esters of glycerol (glycerin), propylene glycol and sorbitol. In some embodiments, the amphiphilic agent is selected from mono- and di-glycerides of C8-C12 saturated fatty acids. In some embodiments, the amphiphilic agent is selected from CAPMUL® MCM, CAPMUL® MCM 8, CAPMUL® MCM 10, IMWITOR® 308, IMWITOR® 624, IMWITOR® 742, IMWITOR® 988, CAPRYOL™ PGMC, CAPRYOL™ 90, LAUROGLYCOL™ 90, CAPTEX® 200, CRILL™ 1, CRILL™ 4, PECEOL® and MAIS INE™ 35-1. In some embodiments, the amphiphilic vehicle further comprises propylene glycol, a propylene glycol- sparing agent (e.g., ethanol or/and glycerol), or an antioxidant (e.g., butylated hydroxyanisole, butylated hydroxytoluene, propyl gallate or/and sodium sulfite), or any combination thereof. In additional embodiments, the amphiphilic vehicle contains on a weight basis about 0.1-5% of the NK1R antagonist (e.g., aprepitant), about 50-90% of the amphiphilic agent, about 5-40% of propylene glycol, about 5-20% of the propylene glycol-sparing agent, and about 0.01-0.5% of the antioxidant.

An NK1R antagonist (e.g., aprepitant) can also be formulated for parenteral administration by injection or infusion to circumvent gastrointestinal absorption and first-pass metabolism. A representative parenteral route is intravenous.

Additional advantages of intravenous administration include direct administration of a therapeutic agent into systemic circulation to achieve a rapid systemic effect, and the ability to administer the agent continuously or/and in a large volume if desired. Formulations for injection or infusion can be in the form of, e.g., solutions, suspensions or emulsions in oily or aqueous vehicles, and can contain excipients such as suspending agents, dispersing agents or/and stabilizing agents. For example, aqueous or non-aqueous (e.g., oily) sterile injection solutions can contain an NK1R antagonist (e.g., aprepitant) along with excipients such as an antioxidant, a buffer, a bacteriostat and solutes that render the formulation isotonic with the blood of the subject. Aqueous or non-aqueous sterile suspensions can contain an NK1R antagonist (e.g., aprepitant) along with excipients such as a suspending agent and a thickening agent, and optionally a stabilizer and an agent that increases the solubility of the NK1R antagonist to allow for the preparation of a more concentrated solution or suspension. As another example, a sterile aqueous solution for injection or infusion (e.g., subcutaneously or intravenously) can contain an NK1R antagonist (e.g., aprepitant), NaCl, a buffering agent (e.g., sodium citrate), a preservative (e.g., meta-cresol), and optionally a base (e.g., NaOH) or/and an acid (e.g., HCl) to adjust pH.

For topical administration, an NK1R antagonist (e.g., aprepitant) can be formulated as, e.g., a buccal or sublingual tablet or pill. Advantages of a buccal or sublingual tablet or pill include avoidance of first-pass metabolism and circumvention of gastrointestinal absorption. A buccal or sublingual tablet or pill can also be designed to provide faster release of the NK-1 antagonist for more rapid uptake of it into systemic circulation. In addition to a therapeutically effective amount of the NK1R antagonist (e.g., aprepitant), the buccal or sublingual tablet or pill can contain suitable excipients, including without limitation any combination of fillers and diluents (e.g., mannitol and sorbitol), binding agents (e.g., sodium carbonate), wetting agents (e.g., sodium carbonate), disintegrants (e.g., crospovidone and croscarmellose sodium), lubricants (e.g., silicon dioxide [including colloidal silicon dioxide] and sodium stearyl fumarate), stabilizers (e.g., sodium bicarbonate), flavoring agents (e.g., spearmint flavor), sweetening agents (e.g., sucralose), and coloring agents (e.g., yellow iron oxide).

For topical administration, an NK1R antagonist (e.g., aprepitant) can also be formulated for intranasal administration. The nasal mucosa provides a big surface area, a porous endothelium, a highly vascular subepithelial layer and a high absorption rate, and hence allows for high bioavailability. Moreover, intranasal administration avoids first-pass metabolism and can introduce a significant concentration of the NK1R antagonist to the central nervous system, allowing the NK1R antagonist to block the central cough reflex via the nucleus tractus solitarius in the cough center in the medulla oblongata, where vagal afferent nerves terminate. An intranasal solution or suspension formulation can comprise an NK1R antagonist (e.g., aprepitant) along with excipients such as a solubility enhancer (e.g., propylene glycol), a humectant (e.g., mannitol or sorbitol), a buffer and water, and optionally a preservative (e.g., benzalkonium chloride), a mucoadhesive agent (e.g., hydroxyethylcellulose) or/and a penetration enhancer. In some embodiments, a nasal spray formulation comprises an NK1R antagonist (e.g., aprepitant), microcrystalline cellulose, sodium carboxymethylcellulose, dextrose and water, and optionally an acid (e.g., HCl) to adjust pH. An intranasal solution or suspension formulation can be administered to the nasal cavity by any suitable means, including but not limited to a dropper, a pipette, or spray using, e.g., a metering atomizing spray pump.

The topical administration can be pulmonary, including by oral inhalation and nasal inhalation. Other suitable topical formulations and dosage forms include without limitation ointments, creams, gels, lotions, pastes and the like.

Ointments are semi-solid preparations that are typically based on petrolatum or a petroleum derivative. Creams are viscous liquids or semi-solid emulsions, either oil-in-water or water-in-oil. Cream bases are water-washable, and contain an oil phase, an emulsifier and an aqueous phase. The oil phase, also called the "internal" phase, generally comprises petrolatum and a fatty alcohol (e.g., cetyl or stearyl alcohol). The aqueous phase typically, although not necessarily, exceeds the oil phase in volume, and usually contains a humectant. The emulsifier in a cream formulation is generally a non-ionic, anionic, cationic or amphoteric surfactant. Gels are semi-solid, suspension-type systems. Single-phase gels contain organic macromolecules (polymers) distributed substantially uniformly throughout the carrier liquid, which is typically aqueous but can also contain an alcohol (e.g., ethanol or isopropanol) and optionally an oil. Lotions are preparations to be applied to the skin surface without friction, and are typically liquid or semi-liquid preparations in which solid particles, including the active agent, are present in a water or alcohol base. Lotions are usually suspensions of finely divided solids and typically contain suspending agents to produce better dispersion as well as compounds useful for localizing and holding the active agent in contact with the skin. Pastes are semi-solid dosage forms in which the active agent is suspended in a suitable base. Depending on the nature of the base, pastes are divided between fatty pastes or those made from single-phase aqueous gels.

Various excipients can be included in a topical formulation. For example, solvents, including a suitable amount of an alcohol, can be used to solubilize the active agent. Other optional excipients include without limitation gelling agents, thickening agents, emulsifiers, surfactants, stabilizers, buffers, antioxidants, preservatives, cooling agents (e.g., menthol), opacifiers, fragrances and colorants. For an active agent having a low rate of permeation through the skin or mucosal tissue, a topical formulation can contain a permeation enhancer to increase the permeation of the active agent through the skin or mucosal tissue. A topical formulation can also contain an irritation-mitigating excipient that reduces any irritation to the skin or mucosa caused by the active agent, the permeation enhancer or any other component of the formulation.

In some embodiments, an NK1R antagonist (e.g., aprepitant) is delivered from a sustained-release composition. As used herein, the term "sustained-release composition" encompasses sustained-release, prolonged-release, extended-release, slow-release and controlled-release compositions, systems and devices. Use of a sustained-release composition can have benefits, such as an improved profile of the amount of the drug or an active metabolite thereof delivered to the target site(s) over a time period, including delivery of a therapeutically effective amount of the drug or an active metabolite thereof over a prolonged time period. In some embodiments, the sustained-release composition delivers the NK1R antagonist over a period of at least about 1 day, 2 days, 3 days, 1 week, 2 weeks, 3 weeks, 1 month, 2 months, 3 months or longer. In some embodiments, the sustained-release composition is a drug-encapsulation system, such as nanoparticles, microparticles or a capsule made of, e.g., a biodegradable polymer or/and a hydrogel. In some embodiments, the sustained-release composition comprises a hydrogel. Non-limiting examples of polymers of which a hydrogel can be composed include polyvinyl alcohol, acrylate polymers (e.g., sodium poly acrylate), and other homopolymers and copolymers having a relatively large number of hydrophilic groups (e.g., hydroxyl or/and carboxylate groups). In other embodiments, the sustained-release drug-encapsulation system comprises a membrane-enclosed reservoir, wherein the reservoir contains a drug and the membrane is permeable to the drug. Such a drug-delivery system can be in the form of, e.g., a transdermal patch.

The sustained-release composition can be an oral dosage form, such as a tablet or capsule. For example, a drug can be embedded in an insoluble porous matrix such that the dissolving drag must make its way out of the matrix before it can be absorbed through the gastrointestinal tract. A drug can be embedded in a matrix that swells to form a gel through which the drug exits. Sustained release can also be achieved by way of a single-layer or multi-layer osmotic controlled-release oral delivery system (OROS). An OROS is a tablet with a semi-permeable outer membrane and one or more small laser- drilled holes in it. As the tablet passes through the body, water is absorbed through the semipermeable membrane via osmosis, and the resulting osmotic pressure pushes the drug out through the hole(s) in the tablet and into the gastrointestinal tract where it can be absorbed.

In some embodiments, the sustained-release composition is formulated as polymeric nanoparticles or microparticles, wherein the polymeric particles can be delivered, e.g., by inhalation or injection or from an implant. In some embodiments, the polymeric implant or polymeric nanoparticles or microparticles are composed of a biodegradable polymer. In some embodiments, the biodegradable polymer comprises lactic acid or/and glycolic acid [e.g., an L-lactic acid-based copolymer, such as poly(L-lactide-co-glycolide) or poly(L-lactic acid-co-D,L-2-hydroxyoctanoic acid)]. For example, biodegradable polymeric microspheres composed of polylactic acid or/and polyglycolic acid can serve as sustained-release pulmonary drug-delivery systems. The biodegradable polymer of the polymeric implant or polymeric nanoparticles or microparticles can be selected so that the polymer substantially completely degrades around the time the period of treatment is expected to end, and so that the byproducts of the polymer's degradation, like the polymer, are biocompatible.

For a delayed or sustained release of an NK1R antagonist (e.g., aprepitant), a composition can also be formulated as a depot that can be implanted in or injected into a subject, e.g., intramuscularly or subcutaneously. A depot formulation can be designed to deliver the NK1R antagonist over a longer period of time, e.g., over a period of at least about 1 week, 2 weeks, 3 weeks, 1 month, 6 weeks, 2 months, 3 months or longer. For example, the NK1R antagonist can be formulated with a polymeric material (e.g., polyethylene glycol (PEG), polylactic acid (PLA) or polyglycolic acid (PGA), or a copolymer thereof (e.g., PLGA)), a hydrophobic material (e.g., as an emulsion in an oil) or/and an ion- exchange resin, or as a sparingly soluble derivative (e.g., a sparingly soluble salt). As an illustrative example, an NK1R antagonist (e.g., aprepitant) can be incorporated or embedded in sustained-release microparticles composed of PLGA and formulated as a monthly depot.

An NK1R antagonist (e.g., aprepitant) can also be contained or dispersed in a matrix material. The matrix material can comprise a polymer (e.g., ethylene-vinyl acetate) and controls the release of the compound by controlling dissolution or/and diffusion of the compound from, e.g., a reservoir, and can enhance the stability of the compound while contained in the reservoir. Such a release system can be designed as a sustained-release system, can be configured as, e.g., a transdermal or transmucosal patch, and can contain an excipient that can accelerate the compound's release, such as a water-swellable material (e.g., a hydrogel) that aids in expelling the compound out of the reservoir. For example, U.S. Pat. Nos. 4,144,317 and 5,797,898 describe examples of such a release system.

The release system can provide a temporally modulated release profile (e.g., pulsatile release) when time variation in plasma levels is desired, or a more continuous or consistent release profile when a constant plasma level is desired. Pulsatile release can be achieved from an individual reservoir or from a plurality of reservoirs. For example, where each reservoir provides a single pulse, multiple pulses ("pulsatile" release) are achieved by temporally staggering the single pulse release from each of multiple reservoirs.

Alternatively, multiple pulses can be achieved from a single reservoir by incorporating several layers of a release system and other materials into a single reservoir. Continuous release can be achieved by incorporating a release system that degrades, dissolves, or allows diffusion of a compound through it over an extended time period. In addition, continuous release can be approximated by releasing several pulses of a compound in rapid succession ("digital" release). An active release system can be used alone or in conjunction with a passive release system, as described in U.S. Pat. No. 5,797,898.

In addition, pharmaceutical compositions comprising an NK1R antagonist (e.g., aprepitant) can be formulated as, e.g., liposomes, micelles (e.g., those composed of biodegradable natural or/and synthetic polymers, such as lactosomes), microspheres, microparticles or nanoparticles, whether or not designed for sustained release. For example, liposomes can be used as sustained release pulmonary drug-delivery systems that deliver drugs to the alveolar surface for treatment of systemic diseases.

The pharmaceutical compositions can be manufactured in any suitable manner known in the art, e.g., by means of conventional mixing, dissolving, suspending, granulating, dragee-making, levigating, emulsifying, encapsulating, entrapping or compressing processes.

A pharmaceutical composition can be presented in unit dosage form as a single dose wherein all active and inactive ingredients are combined in a suitable system, and components do not need to be mixed to form the composition to be administered. The unit dosage form can contain an effective dose, or an appropriate fraction thereof, of a therapeutic agent (e.g., an NK1R antagonist, such as aprepitant). Representative examples of a unit dosage form include a tablet, capsule or pill for oral administration, and powder in a vial or ampoule for oral or nasal inhalation.

Alternatively, a pharmaceutical composition can be presented as a kit, wherein the active ingredient, excipients and carriers (e.g., solvents) are provided in two or more separate containers (e.g., ampoules, vials, tubes, bottles or syringes) and need to be combined to form the composition to be administered. The kit can contain instructions for storing, preparing and administering the composition (e.g., a solution to be injected intravenously).

A kit can contain all active and inactive ingredients in unit dosage form or the active ingredient and inactive ingredients in two or more separate containers, and can contain instructions for using the pharmaceutical composition.

In some embodiments, a kit contains an NK1R antagonist (e.g., aprepitant) or a pharmaceutically acceptable salt, solvate, hydrate, clathrate, polymorph, prodrug or metabolite thereof, and instructions for administering the compound. In some embodiments, the compound is contained or incorporated in, or provided by, a device or system configured for pulmonary delivery of the compound by oral inhalation, such as a metered-dose inhaler, a dry powder inhaler or a nebulizer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In some embodiments, a dispenser designed to dispense the daily doses one at a time in the order of their intended use is provided. For example, the dispenser is equipped with a memory aid, so as to further facilitate compliance with the regimen. An example of such a memory aid is a mechanical counter which indicates the number of daily doses that has been dispensed. Another example of such a memory aid is a battery-powered micro-chip memory coupled with a liquid crystal readout, or audible reminder signal which, for example, reads out the date that the last daily dose has been taken and/or reminds one when the next dose is to be taken.

Oral or nasal inhalation can be achieved by means of, e.g., a metered-dose inhaler (MDI), a nebulizer or a dry powder inhaler (DPI). For example, an NK1R antagonist (e.g., aprepitant) can be formulated for aerosol administration to the respiratory tract by oral or nasal inhalation. The drug is delivered in a small particle size (e.g., between about 0.5 micron and about 5 microns), which can be obtained by micronization, to improve, e.g., drug deposition in the lungs and drug suspension stability. The drug can be provided in a pressurized pack with a suitable propellant, such as a hydrofluoroalkane (HFA, e.g., 1,1,1,2-tetrafluoroethane [HFA-134a]), a chlorofluorocarbon (CFC, e.g., dichlorodifluoromethane, trichlorofluoromethane or dichlorotetrafluoroethane), or a suitable gas (e.g., oxygen, compressed air or carbon dioxide). The drug in the aerosol formulation is dissolved, or more often suspended, in the propellant for delivery to the lungs. The aerosol can contain excipients such as a surfactant (which enhances penetration into the lungs by reducing the high surface tension forces at the air-water interface within the alveoli, may also emulsify, solubilize or/and stabilize the drug, and can be, e.g., a phospholipid such as lecithin) or/and a stabilizer. For example, an MDI formulation can comprise an NK1R antagonist (e.g., aprepitant), a propellant (e.g., an HFA such as 1,1,1,2-tetrafluoroethane), a surfactant (e.g., a fatty acid such as oleic acid), and a co-solvent (e.g., an alcohol such as ethanol). The MDI formulation can optionally contain a dissolved gas (e.g., $CO_2$). After device actuation, the bursting of $CO_2$ bubbles within the emitted aerosol droplets breaks up the droplets into smaller droplets, thereby increasing the respirable fraction of drug. As another example, a nebulizer formulation can comprise an NK1R antagonist (e.g., aprepitant), a surfactant (e.g., a Tween® such as polysorbate 80), a chelator or preservative (e.g., edetate disodium), an isotonicity agent (e.g., sodium chloride), pH buffering agents (e.g., citric acid/sodium citrate), and water. The drug can be delivered by means of, e.g., a nebulizer or an MDI with or without a spacer, and the drug dose delivered can be controlled by a metering chamber (nebulizer) or a metering valve (MDI).

For oral or nasal inhalation using a dry powder inhaler (DPI), an NK1R antagonist (e.g., aprepitant) can be provided in the form of a dry micronized powder, where the drug particles are of a certain small size (e.g., between about 0.5 micron and about 5 microns) to improve, e.g., aerodynamic properties of the dispersed powder and drug deposition in the lungs. Particles between about 0.5 micron and about 5 microns deposit by sedimentation in the terminal bronchioles and the alveolar regions. By contrast, the majority of larger particles (>5 microns) do not follow the stream of air into the many bifurcations of the airways, but rather deposit by impaction in the upper airways, including the oropharyngeal region of the throat. A DPI formulation can contain the drug particles alone or blended with a powder of a suitable larger base/carrier, such as lactose, starch, a starch derivative (e.g., hydroxypropylmethyl cellulose) or polyvinylpyrrolidine. The carrier particles enhance flow, reduce aggregation, improve dose uniformity and aid in dispersion of the drug particles. A DPI formulation can optionally contain an excipient such as magnesium stearate or/and leucine that improves the performance of the formulation by interfering with inter-particle bonding (by anti-adherent action). The powder formulation can be provided in unit dose form, such as a capsule (e.g., a gelatin capsule) or a cartridge in a blister pack, which can be manually loaded or pre-loaded in an inhaler. The drug particles can be drawn into the lungs by placing the mouthpiece or nosepiece of the inhaler into the mouth or nose, taking a sharp, deep inhalation to create turbulent airflow, and holding the breath for a period of time (e.g., about 5-10 seconds) to allow the drug particles to settle down in the bronchioles and the alveolar regions.

Lactose (e.g., alpha-lactose monohydrate) is the most commonly used carrier in DPI formulations. Other carriers for DPI formulations include without limitation glucose, mannitol (e.g., crystallized mannitol [Pearlitol 110 C] and spray-dried mannitol [Pearlitol 100 SD]), maltitol (e.g., crystallized maltitol [Maltisorb P90]), sorbitol and xylitol.

Dry powder inhalers can be classified by dose type into single-unit dose (including disposable and reusable) and multi-dose (including multi-dose reservoirs and multi-unit dose). In a single-unit dose DPI, the formulation can be a powder mix of a micronized drug powder and a carrier and can be supplied in individual capsules, which are inserted into the inhaler for a single dose and are removed and discarded after use. The capsule body containing the dose falls into the device, while the cap is retained in the entry port for subsequent disposal. As the user inhales, the portion of the capsule containing the drug experiences erratic motion in the airstream, causing dislodged particles to be entrained and subsequently inhaled. Particle de-aggregation is caused mainly by turbulence promoted by the grid upstream of the mouthpiece or nosepiece. Examples of single-unit dose DPIs include without limitation Aerolizer®, AIR®, Conix One® (foil seal), Diskhaler®, Diskus®, Handihaler®, Microhaler®, Rotahaler® and Turbo spin®.

EXAMPLES

Some aspects of the embodiments discussed above are disclosed in further detail in the following examples, which are not in any way intended to limit the scope of the present disclosure.

Example 1

A Method of Treating Alzheimer's Disease

A subject suffering from Alzheimer's disease (AD) is identified. The subject is then orally administered about 10-100 mg (e.g., about 10 mg, 20 mg, 30 mg, 40 mg, 50 mg, 60 mg, 70 mg, 80 mg, 90 mg or 100 mg) of a composition comprising aprepitant or a pharmaceutically acceptable salt, solvate, stereoisomer thereof as the sole therapeutic agent, twice a day. The subject is monitored for symptoms of AD.

Example 2

A Method of Delaying or Reducing the Likelihood of Onset of Alzheimer's Disease A subject that is at a risk of suffering from Alzheimer's disease (AD) is identified. The subject is then orally administered about 10-100 mg (e.g., about 10 mg, 20 mg, 30 mg, 40 mg, 50 mg, 60 mg, 70 mg, 80 mg, 90 mg or 100 mg) of a composition comprising aprepitant or a pharmaceutically acceptable salt, solvate, stereoisomer, or prodrug thereof as the sole therapeutic agent, twice a day. The subject is monitored for symptoms of AD.

Example 3

A Method of Delaying or Reversing the Progression of Alzheimer's Disease

A subject suffering from Alzheimer's disease (AD) is identified. The subject is then orally administered about 10-100 mg (e.g., about 10 mg, 20 mg, 30 mg, 40 mg, 50 mg, 60 mg, 70 mg, 80 mg, 90 mg or 100 mg) of a composition comprising aprepitant or a pharmaceutically acceptable salt, solvate, stereoisomer, or prodrug thereof as the sole therapeutic agent, twice a day. The subject is monitored for symptoms of AD.

Example 4

A Method of Treating, Preventing, or Reversing Cognitive Decline in Clinical or Pre-Clinical Alzheimer's Disease A subject that is at a risk of suffering from AD or is suffering from AD is identified. The subject is then orally administered about 10-100 mg (e.g., about 10 mg, 20 mg, 30 mg, 40 mg, 50 mg, 60 mg, 70 mg, 80 mg, 90 mg or 100 mg) of a composition comprising aprepitant or a pharmaceutically acceptable salt, solvate, stereoisomer, or prodrug thereof as the sole therapeutic agent, twice a day. The subject is monitored for symptoms of AD.

Example 5

Demonstration of the Effects of Aprepitant on Improving Memory in a Mouse Model of Alzheimer's Disease Experiments in this example is carried out to demonstrate if aprepitant can improve memory in a mouse model of Alzheimer's disease.

APP/PS1$^{+/-}$ and littermate wildtype (WT) mice are utilized in this example. This mouse model begins to develop observed AP plaques at around 5 months of age. At 9 months of age, mice can undergo behavioral testing for 1 month with sacrifice at 10 months of age for histological analysis. To determine if aprepitant can improve memory in this mouse model, mice can begin treatment with aprepitant (e.g., 40 mg/kg via oral administration) 3 weeks prior to behavioral testing and continuing treatment through testing. Wildtype mice do not contain Aβ pathology at any age but are necessary in the behavioral analysis to identify aprepitant-specific effects.

For example, a study can include 5 groups of animals: 1) APP/PS1$^{+/-}$ mice, 12 males and 12 females, treated with vehicle; 2) APP/PS1$^{+/-}$ mice, 12 males and 12 females, treated with aprepitant; 3) wildtype littermate mice, 12 male and 12 females, treated with vehicle; 4) wildtype littermate mice, 12 male and 12 females, treated with aprepitant; and 5) APP/PS1$^{+/-}$ mice, 8 males and 8 females, sacrificed at beginning of the study.

Mice can be assessed in a range of behavioral tests to determine the scope of behaviors affected by chronic aprepitant treatment. By 9 months of age, untreated APP/PS1$^{+/-}$ mice have impaired performance on tests of learning and memory (Cao et al, 2007). Spatial learning and memory can be measured in all mice using a water maze test. Morris Water maze is a standard learning and memory test used in many mouse models of AD.. To evaluate other forms of memory, influences of chronic aprepitant treatment on non-spatial memory can also be determined using a novel object recognition and novel object location task. These tests allow assessment of both hippocampal and non-hippocampal dependent memory.

General locomotor activity, emotionality (anxiety), habituation, coordination and balance, and motor function can be evaluated to determine effects of aprepitant treatment on these measures in APP/PS1$^{+/-}$ and wildtype mice, and to control for differences in these parameters on interpretation of cognitive results.

Sacrificing a cohort of mice at the beginning of the study can enable one to determine if the chronic administration of drug either prevented, slowed, or reversed pathology. A variety of brain regions can be harvested for analysis. Mice can be anesthetized with sodium pentobarbital, then have a cardiac bleed to obtain plasma followed by cardiac perfusion with saline to eliminate blood. The brain can be removed. For example, one hemisphere can be post-fixed in paraformaldehyde and processed for histological analysis of Aβ burden while the other hemisphere can be microdissected into the striatum, cerebellum, hippocampus, and cortex then snap frozen on dry ice for future biochemical analysis of Aβ40, Aβ42, and tau levels as performed in published methods.

Example 6

Demonstration of the Effects of Aprepitant on Aβ Levels in a Mouse Model of Alzheimer's Disease This example demonstrates the effect of a peripherally-administered NK1R antagonist treatment (e.g., aprepitant) on brain interstitial fluid (ISF) Aβ levels in living mice. In vivo microdialysis was utilized to measure the basal concentration of ISF Aβ in each mouse, followed by administration via oral gavage of 40 mg/kg dose of aprepitant or vehicle (corn oil) and continued measurement of Aβ over 24 hours.

Three-four month old APP/PS1$^{+/-}$ mice were implanted with unilateral guide cannula above the hippocampus followed by insertion of microdialysis probes (see, for example, In Vivo AβMicrodialysis of Example 7). Each animal recovered for 3 days between guide cannula implantation and start of microdialysis. Littermate females and males were separated randomly into each treatment group. Throughout each microdialysis study, mice were housed in special RaTurn caging systems to provide freedom of movement and ad lib food and water while the microdialysis equipment was attached. Mice recovered for at least 12 hours after microdialysis probe insertion followed by four 90-minute samples of ISF to establish baseline ISF AP levels in each mouse (mean of this 6 hour period is "basal ISF AP concentration in each mouse"). Mice were then administered by oral gavage either aprepitant (40 mg/kg) or vehicle.

Following drug administration, ISF was measured every 60 minutes for 24 hours. At the end of each study, animals were sacrificed and brains removed. The ipsilateral hemisphere with the microdialysis probe was processed for histological verification of probe placement and the contralateral hemisphere was snap frozen on dry ice and stored at −80° C. for future biochemical analyses. ISF APβ was immediately measured at the end of each study by Aβ sandwich ELISA. The standard ELISA coats the microtiter plate with mouse-anti-Aβ mHJ2 and detects with biotinylated mouse-anti-Aβ mHJ5.1.

FIG. 1 depicts non-limiting exemplary microdialysis data showing the ISF levels in the aprepitant treated group compared to the vehicle treated group. The comparisons show that the ISF AP levels in the aprepitant treated group significantly decreased from their baseline (***p <0.0001), while vehicle treated mice did not (p=0.4003).

Figure 2:
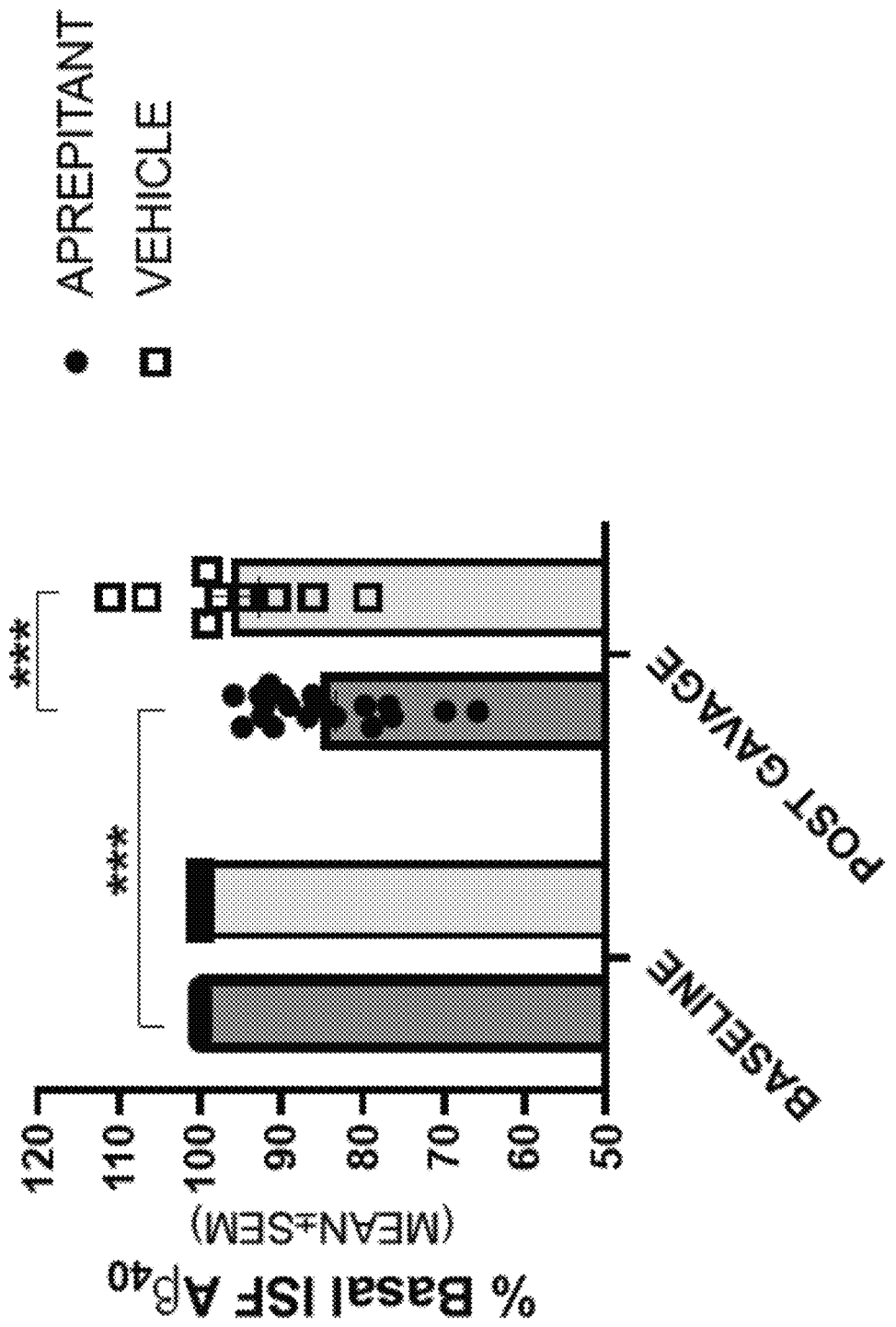
FIG. 2 depicts non-limiting exemplary data from a study as described in Example 6 showing average ISF Aβ levels post gavage in the aprepitant treated group compared to the vehicle treated group and the baseline.

FIG. 2 depicts non-limiting exemplary data showing average ISF Aβ levels post gavage in the aprepitant treated group compared to the vehicle treated group and the baseline. The data demonstrates that aprepitant treated mice have significantly lower average ISF Aβ levels post gavage compared to vehicle treated mice (***p=0.0002).

Example 7

Demonstration of the Effects of Aprepitant on Memory Improvement in a Mouse Model of Alzheimer's Disease This example demonstrates the effect of aprepitant on memory improvement in a mouse model of Alzheimer's disease based on a Morris Water Maze test.

Figure 3A:
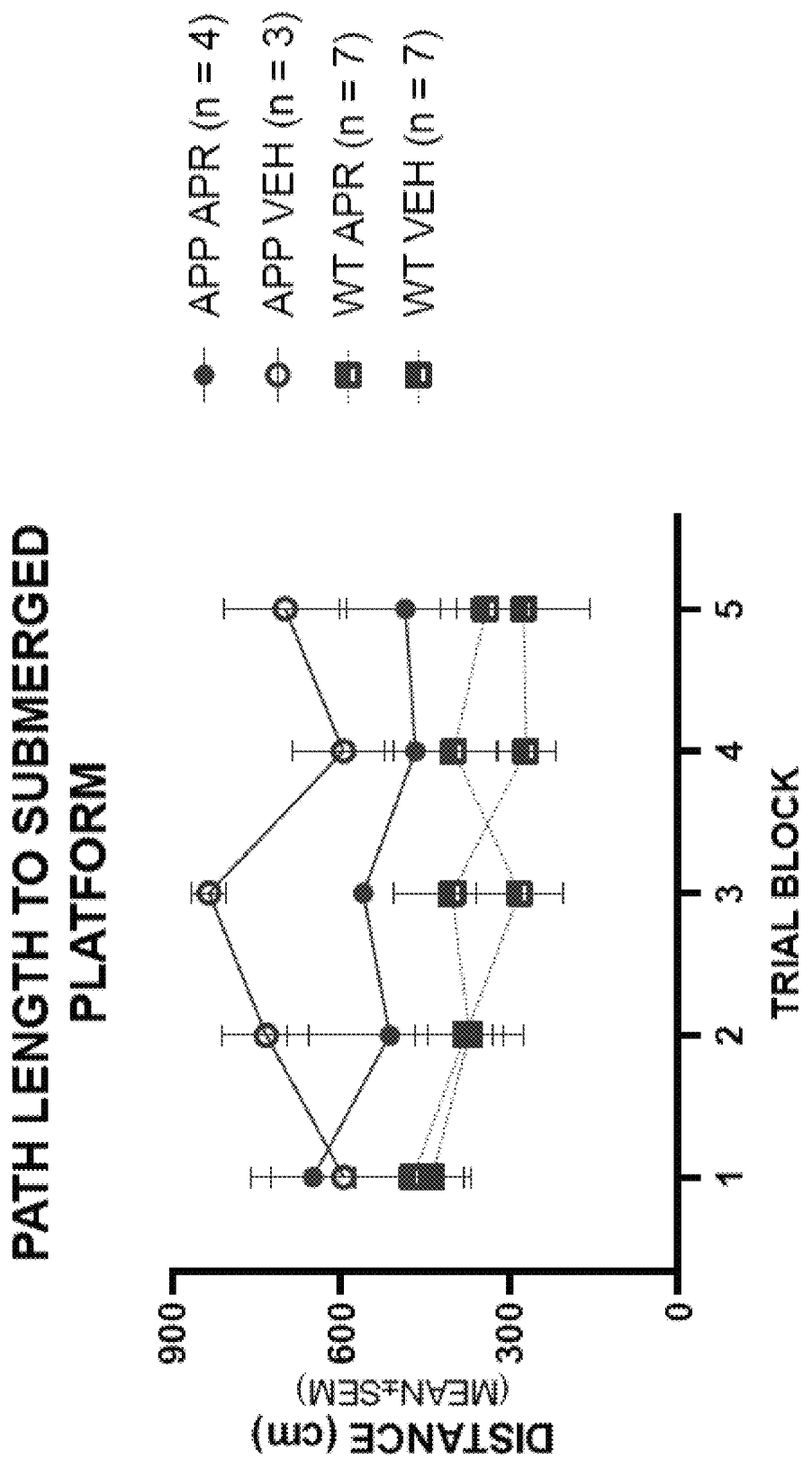
FIGS. 3A-B depict non-limiting exemplary data from a Morris Water Maze study described in Example 5 showing spatial learning and memory after 3 weeks treatment with oral aprepitant or vehicle in APP/PS1 or wild type (WT) mice.
Figure 3B:
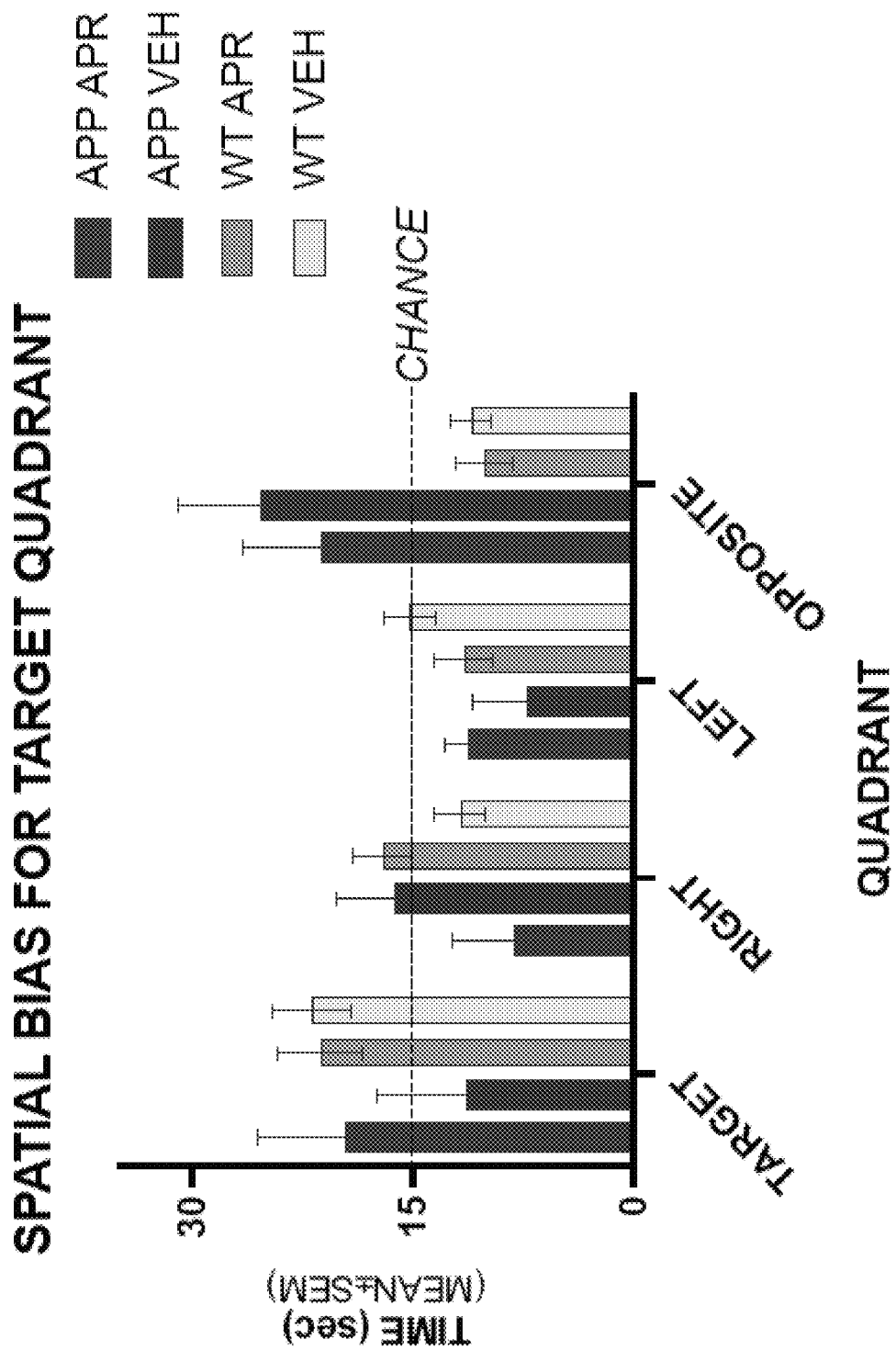

A Morris Water Maze test was used to evaluate spatial learning and memory after 3 weeks treatment with oral aprepitant or vehicle in APP/PS1 or wild type (WT) mice. APP/PS1 mice receiving vehicle (n=3; 2 males and 1 female) showed a longer path length trend overall compared to the APP/PS1 mice receiving treatment with aprepitant (n=4; 2 each sex) and the WT mice receiving either aprepitant (n=7; 4 female and 3 male) or vehicle (n=7; 4 females and 3 males) suggesting that aprepitant improved spatial learning in the APP/PS1 mice (FIG. 3A). In a probe trial conducted at the end of the learning trials to evaluate spatial memory, the aprepitant-treated APP/PS1 mice showed a trend for improved memory for the platform location compared to the vehicle-treated APP/PS1 mice based on the time spent in the target quadrant (FIG. 3B).

Example 8

Exemplary Materials and Methods

The following exemplary materials and methods can be used to practice Example 5 described above, and were used to practice Example 6-7 described above.

Animal Model. All experiment protocols using animals were performed ethically and in accordance with the guidelines established by the Institutional Animal Care and Use Committee at Washington University. APPswe/PS1DE9 hemizygous mice (Jackson Laboratory, RRID: MMRRC_034829.JAX) (Savonenko et al., 2003) were bred to wild type C3H/B6 mice and aged the APP/PS1$^{+/-}$ offspring to 2-3.5 months for microdialysis experiments or aged to 9 months for behavioral testing. Males and females were included in each group; aprepitant treated mice n=20 (11 males, 9 females), Vehicle treated mice n=10 (6 males, 3 females) for microdialysis experiments. Preliminary data presented for the behavioral testing (Morris Water Maze) includes APP/PS1$^{+/-}$ mice treated with aprepitant (n=4; 2 each sex) or vehicle (2 males and 1 female) and wild type mice (n=7; 4 female and 3 male for each treatment group, 14 total).

In Vivo Aβ Microdialysis. In vivo microdialysis to measure brain ISF Aμ in the hippocampus of freely moving APP/PS1 mice was performed similar to previously described (Cirrito et al., 2003, Yuede et al. 2020). This method captures soluble molecules in the extracellular fluid that are below the 38 kDa molecular weight cutoff of the probes. Under volatile isoflurane anesthetic, guide cannula (BR-style; Bioanalytical Systems) were cemented above the left hippocampus (3.1 mm behind bregma, 2.5 mm lateral to midline, and 1.2 mm below dura at a 12° angle). Two millimeter microdialysis probes were inserted through the guides so their membranes were completely contained in the hippocampus (38 kDa BR-2; Bioanalytical Systems). Microdialysis buffer was aCSF (perfusion buffer in mM: 1.3 $CaCl_2$, 1.2 $MgSO_4$, 3 KCl, 0.4 $KH_2PO_4$, and 122 NaCl, pH 7.35) containing 0.15% bovine serum albumin (BSA) (Sigma-Aldrich) that was filtered through a 0.22 μM membrane. The flow rate was 1.0 μL/min. Samples were collected every 60 or 90 minutes into a refrigerated fraction collector (Univentor Limited) in polypropylene tubes and assessed for Mx-40 by sandwich ELISA. Normalized basal ISF Aβ levels were defined as the mean concentration of Aβ over the 7.5 hours preceding drug administration. All Aβ values were normalized to the basal Aβ concentration for each animal. After establishing baseline ISF aprepitant (40 mg/kg) or vehicle (corn oil) was administered by oral gavage.

Aβ Sandwich ELISA. ISF Aβx-40 levels were measured using sandwich ELISAs as described (Hettinger et al., 2018). This ELISA detects both human and murine Aβ. A mouse anti-Aβ40 antibody (mHJ2; 10 μg/ml) against the C-terminus of Aβ was used to capture peptides and a biotinylated central domain antibody (mHJ5.1; 75 ng/ml) was used to detect them. This was followed by a streptavidin poly-HRP-40 assay to measure Aβ concentration (Fitzgerald Industries). All steps included washes with PBS containing 0.05% Tween-20. The standard curve for the ELISA was recombinant Aβ-40 (Anaspec) taken from a stock in formic acid to remove preformed aggregates. ELISA sample buffers included sufficient Tris to neutralize pH of the formic acid. ELISAs were developed using Super Slow ELISA TMB (Sigma-Aldrich) and absorbance read on a Bio-Tek Epoch plate reader at 650 nm.

Statistical Analysis. All statistical analyses were performed using Graphpad Prism v9.0 for MacOS. Using the ROUT method in Graphpad, 1 mouse was identified as an outlier and removed from the data set (male mouse; aprepitant treatment group). Data were screened for normality of distribution using the Shapiro-Wilk and Kolmogorov-Smirnov tests. Average changes from baseline in ISF AP were evaluated using 2-way Repeated Measures ANOVA with main factors of Treatment and Time. There is a significant interaction between factors; Treatment×Time [$F(1, 26) = 9.145$, $p=0.0056$). Bonferroni post hoc comparisons show aprepitant treated mice have significantly lower average ISF Aβ levels post gavage compared to vehicle treated mice (*$p=0.0002$). Within group comparisons show the ISF Aβ levels in the aprepitant treated group significantly decreased from their baseline (*$p <0.0001$), while vehicle treated mice did not ($p=0.4003$).

Morris water maze (MWM) test. MWM was conducted as described in Wozniak et al., 2004. Briefly, cued, place and probe trials were conducted in a galvanized steel pool, measuring 120 cm in diameter, and filled with opaque water (diluted nontoxic white tempera paint). The PVC escape platform measured 11.5 cm in diameter. A digital video camera connected to a PC computer and the computer software program ANY-maze (Stoelting Co., Wood Dale, IL) tracked the swimming pathway of the mouse to the escape platform and quantified path length, latency to find escape platform, and swimming speeds. On two consecutive days, animals received four cued trials to habituate mice to the swimming task procedure and control for any differences in swimming, visual, or motivational performance in the test. A red tennis ball atop a rod was attached to the escape platform and served as a visual cue for the platform. To prevent spatial learning, the escape platform was moved to a different quadrant location for each trial. The mouse was released from the quadrant opposite to the platform location and allowed 60s to locate the platform. Once the mouse found the platform, it was allowed to remain there for lOs before being returned to its home cage. Three days following visible platform testing, the cue was removed from the platform, and it was submerged 1 cm under the water for the hidden platform tests to evaluate spatial learning. Animals received two blocks of two consecutive trials on five consecutive days, with an inter-trial interval between 30-90s and approximately 2 hr separating trial blocks. The escape platform remained in the same quadrant location for all trials and distal cues were placed on the walls of the room to support spatial learning. The mouse was released from a different location for each trial on each day. The mouse was allowed 60s to find the escape platform and allowed to sit on it for lOs before being returned to its home cage. Cued and hidden platform trials were combined into blocks of two or four trials for analyses, respectively. One hour following completion of hidden platform trials on the 5th day of training, the escape platform was removed from the pool and one 60s probe trial was conducted to assess memory retention for the location of the platform In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of treating Alzheimer's disease (AD) in a subject, comprising administering to the subject in need thereof a therapeutically effective amount of a composition consisting of aprepitant or a pharmaceutically acceptable salt, solvate, stereoisomer, or prodrug thereof, and one or more excipients, thereby treating AD or at least one symptom thereof in the subject; wherein the subject is diagnosed with early stage Alzheimer's disease (AD), mid-stage AD, or late-stage AD, and
  wherein the composition is administered over a period of at least about 6 weeks.

2. A method of treating dementia of the Alzheimer's type in a subject, comprising administering to the subject in need thereof a therapeutically effective amount of a composition consisting of aprepitant or a pharmaceutically acceptable salt, solvate, stereoisomer, or prodrug thereof, and one or more excipients, thereby treating the dementia or at least one symptom thereof in the subject; wherein the subject is diagnosed with early stage Alzheimer's disease (AD), mid-stage AD, or late-stage AD, and
  wherein the composition is administered over a period of at least about 6 weeks.

3. A method of delaying progression of Alzheimer's disease (AD) in a subject, comprising administering to the subject in need thereof a therapeutically effective amount of a composition consisting of aprepitant or a pharmaceutically acceptable salt, solvate, stereoisomer, or prodrug thereof, and one or more excipients, thereby delaying the progression of AD in the subject or at least one symptom thereof; wherein the subject has Alzheimer's disease, and
  wherein the composition is administered over a period of at least about 6 weeks.

4. The method of claim 1, wherein the subject is a human.

5. The method of claim 1, wherein said Alzheimer's disease is sporadic Alzheimer's disease.

6. The method of claim 1, wherein said Alzheimer's disease is familial AD.

7. The method of claim 1, wherein the subject is diagnosed with at least one of mild cognitive impairment associated with Alzheimer's disease (AD) or dementia of Alzheimer's type.

8. The method of claim 1, wherein the composition is administered to the subject by intravenous administration, nasal administration, pulmonary administration, oral administration, parenteral administration, or nebulization.

9. The method of claim 1, wherein the composition is in a form of powder, tablet, capsule, film, disintegrating tablet, liquid, aerosols, or nanoparticles.

10. The method of claim 1, wherein the composition is administered to the subject once, twice, or three times a day.

11. The method of claim 1, wherein the composition is administered to the subject once every day, every two days, or every three days.

12. The method of claim 1, wherein the composition is administered to the subject at a daily dose of 10 mg to 250 mg of aprepitant or a pharmaceutically acceptable salt, solvate, stereoisomer, or prodrug thereof.

13. The method of claim 1, wherein the administering of the composition reduces at least one of formation of plaques, a rate and/or an amount of amyloid fibril formation, amyloid-induced cellular toxicity, amyloid-induced microglial activation, amyloid-induced neurotoxicity, a rate and/or an amount of amyloid aggregation, a rate and/or an amount of amyloid deposition, a degree of amyloid deposition, amyloid-induced inflammation, neuroinflammation, a rate of formation and/or an amount of tangles containing hyperphosphorylated tau, and a concentration and/or an amount of phosphorylated tau.

14. The method of claim 13, wherein the administering of the composition reduces the rate or amount of amyloid aggregation, fibril formation, or deposition.

15. The method of claim 13, wherein the administering of the composition lessens the degree of amyloid deposition, reduces amyloid-induced inflammation, results in reduction of neuroinflammation, or a combination thereof.

16. The method of claim 15, wherein the reduction of neuroinflammation comprises reduction in at least one of cell signaling molecule production, activation of glia, activation of glial activation pathways and responses, proinflammatory cytokines, proinflammatory chemokines, oxidative stress-related responses, acute phase proteins, components of the complement cascade, protein kinase activity, cell damage, and cell death signal transduction pathways.

17. The method of claim 1, wherein the method treats at least one Alzheimer's disease (AD) symptom by at least about 10%.

18. The method of claim 3, wherein the progression of Alzheimer's disease (AD) or symptom thereof is delayed by at least about 5% relative to the subject prior to administration of the composition.

19. The method of claim 3, wherein the progression of Alzheimer's disease (AD) is measured quantitatively and/or qualitatively by at least one technique selected from the group consisting of electroencephalogram (EEG), neuroimaging, functional MRI, structural MRI, diffusion tensor imaging (DTI), [18F] fluorodeoxyglucose (FDG) PET, agents that label amyloid beta or tau, [18F] F-dopa PET, radiotracer imaging, volumetric analysis of regional tissue loss, specific imaging markers of abnormal protein deposition, multimodal imaging, and biomarker analysis (plasma or cerebrospinal fluid).

20. The method of claim 1, wherein the Alzheimer's disease (AD) symptom is selected from the group consisting of:
  (a) a symptom from the Integrated Alzheimer's Disease Rating Scale (iADRS) selected from the group consisting of personal belonging management, selection of clothes, ability to dress self, ability to clean habitation, financial management ability, writing ability, ability to keep appointments, ability to use telephone, ability to prepare food for self, travel ability, awareness of current events, reading ability, interest in television, ability to shop for self, ability to remain alone, ability to perform chores, ability to perform a hobby or game, driving ability, self-management of medications, ability to initiate and finish complex tasks, ability to initiate and finish simple tasks, and any combination thereof;
  (b) a symptom from the Alzheimer's Disease Assessment Scale-Cognitive subscale (ADAS-Cog) selected from the group consisting of learning, naming, command following, ideational praxis, constructional praxis, orientation, recognition memory, and any combination thereof;
  (c) a symptom from the Alzheimer's Disease Cooperative Study-instrumental Activities of Daily Living (ADCS-iADL) wherein the symptom is any of the symptoms recited in (a), (b), and any combination thereof;
  (d) constipation;
  (e) depression;
  (f) cognitive impairment;
  (g) short term memory impairment;
  (h) long term memory impairment;
  (i) concentration impairment;
  (j) coordination impairment;
  (k) mobility impairment;
  (l) speech impairment;
  (m) mental confusion;
  (n) sleep problem, sleep disorder, or sleep disturbance;
  (o) circadian rhythm dysfunction;
  (p) REM disturbed sleep;
  (q) REM behavior disorder;
  (r) hallucinations;
  (s) fatigue;
  (t) apathy;
  (u) erectile dysfunction;
  (v) mood swings;
  (w) urinary incontinence;
  (x) mild cognitive impairment;
  (y) neurodegeneration, and any combination thereof.

21. The method of claim 1, wherein the Alzheimer's disease (AD) symptom is depression and wherein
  the method results in an improvement in the subject's depression over a defined period of time, as measured by at least one clinically-recognized depression rating scale, and
  wherein the defined period of time about 1 day to about 12 months.

22. The method of claim 1, wherein the Alzheimer's disease (AD) symptom is cognitive impairment, and wherein
  progression or onset of the cognitive impairment is slowed, halted, or reversed over a defined period of time following administration of the composition, as measured by a medically-recognized technique, and wherein
  the defined period of time is about 1 day to about 12 months.

23. The method of claim 1, wherein the Alzheimer's disease (AD) symptom is neurodegeneration, and wherein
  the method results in treating, preventing, and/or delaying the progression and/or onset of neurodegeneration in the subject.

24. A kit, comprising
  a therapeutically effective amount of a composition consisting of aprepitant or a pharmaceutically acceptable salt, solvate, stereoisomer, or prodrug thereof, and one or more excipients, wherein the composition is administered over a period of at least about 6 weeks; and
  a label indicating at least one of:
    (a) the kit is for delaying the progression of Alzheimer's disease (AD),
    (b) the kit is for treating Alzheimer's disease (AD),
    (c) the kit is for treating dementia of Alzheimer's type,
    (d) the kit is for treating mild cognitive impairment associated with Alzheimer's disease (AD) and
    (e) the kit is for reversing the progression of Alzheimer's disease (AD).

25. A method of reversing the progression of Alzheimer's disease (AD) in a subject, comprising administering to the subject in need thereof a therapeutically effective amount of a composition consisting of aprepitant or a pharmaceutically acceptable salt, solvate, stereoisomer, or prodrug thereof, and one or more excipients, thereby reversing the progression of AD in the subject; wherein wherein the subject is diagnosed with early stage Alzheimer's disease (AD), mid-stage AD, or late-stage AD,
  wherein the composition is administered over a period of at least about 6 weeks.

26. A method of treating mild cognitive impairment associated with Alzheimer's disease (AD) in a subject, comprising administering to the subject in need thereof a therapeutically effective amount of a composition consisting of aprepitant or a pharmaceutically acceptable salt, solvate, stereoisomer, or prodrug thereof, and one or more excipients, thereby treating the mild cognitive impairment or at least one symptom thereof in the subject; wherein the subject is diagnosed with early stage Alzheimer's disease (AD), mid-stage AD, or late-stage AD, and
  wherein the composition is administered over a period of at least about 6 weeks.

27. The method of claim 25, wherein the progression of Alzheimer's disease (AD) is measured quantitatively and/or qualitatively by at least one technique selected from the group consisting of electroencephalogram (EEG), neuroimaging, functional MRI, structural MRI, diffusion tensor imaging (DTI), [18F] fluorodeoxyglucose (FDG) PET, agents that label amyloid beta or tau, [18F] F-dopa PET, radiotracer imaging, volumetric analysis of regional tissue loss, specific imaging markers of abnormal protein deposition, multimodal imaging, and biomarker analysis (plasma or cerebrospinal fluid).

* * * * *